United States Patent
Gyuris et al.

(10) Patent No.: US 11,897,948 B2
(45) Date of Patent: Feb. 13, 2024

(54) TREATMENT OF CHRONIC KIDNEY DISEASE AND OTHER RENAL DYSFUNCTION USING A GDF15 MODULATOR

(71) Applicant: AVEO Pharmaceuticals, Inc., Cambridge, MA (US)

(72) Inventors: Jeno Gyuris, Lincoln, MA (US); Lorena Lerner, Newton Centre, MA (US)

(73) Assignee: AVEO Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 16/179,166

(22) Filed: Nov. 2, 2018

(65) Prior Publication Data

US 2019/0292252 A1    Sep. 26, 2019

Related U.S. Application Data

(63) Continuation of application No. 15/320,101, filed as application No. PCT/US2015/036794 on Jun. 19, 2015, now abandoned.

(60) Provisional application No. 62/015,242, filed on Jun. 20, 2014.

(51) Int. Cl.
*A61K 39/00* (2006.01)
*C07K 16/22* (2006.01)
*C07K 14/475* (2006.01)

(52) U.S. Cl.
CPC .......... *C07K 16/22* (2013.01); *C07K 14/475* (2013.01); *A61K 2039/505* (2013.01); *C07K 2317/76* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,919,084 B2 | 4/2011 | Breit et al. | |
| 9,175,076 B2 | 11/2015 | Lerner et al. | |
| 9,725,505 B2* | 8/2017 | Lerner | A61P 3/02 |
| 2009/0004181 A1* | 1/2009 | Breit | A61K 38/1709 424/133.1 |
| 2014/0193427 A1 | 7/2014 | Lerner et al. | |

FOREIGN PATENT DOCUMENTS

| | | | |
|---|---|---|---|
| WO | WO-2005/099746 A1 | 10/2005 | |
| WO | WO-2009021293 A1 | 2/2009 | |
| WO | WO-2009038533 A1 | 3/2009 | |
| WO | WO-2009/046495 A1 | 4/2009 | |
| WO | WO 2010/048670 A1 * | 5/2010 | |
| WO | WO-2010/048670 A1 | 5/2010 | |
| WO | WO-2014/049087 A1 | 4/2014 | |
| WO | WO-2014/100689 A1 | 6/2014 | |

OTHER PUBLICATIONS

Feldman, 2002, Molecular Pharmacology. 61(4): 707-709.*
Janigro (2008, Epilepsy Currents 8(1): 23-24).*
Ho et al. (2013, Clin. Chem. 59:1613-1620).*
Abulizi et al. (2017, Sci. Rep. 7(1): 1037; pp. 1-10).*
Zimmer et al. (2005, Shock 23(6):543-548).*
Mazagova et al. (2013, Am. J. Physiol. Renal Physiol. 305:F1249-F1264).*
Breit et al. (2012, Nephrol. Dial. Transplant. 27:70-75).*
Levey et al. (2009, Am. J. Kidney Dis. 53(3):S4-S16).*
Borges et al. (2009, J. Clin. Hypertension 11(5):253-259).*
Wish (2006, Clin. J. Am. Soc. Nephrol. 1:S4-S8).*
Wen et al. (2013, PLOS ONE 8(5), e64025, pp. 1-6).*
Anonymous, (2002), 'Clinical Practice Guidelines K/DOQI for Chronic Kidney Disease: Evaluation, Classification and Stratification,' National Kidney Foundation (Pub), retrieved at https://www.kidney.org/sites/default/files/doc/ckd_evaluation_calssification_stratification.pdf XP055228029.
"Blood Urea Nitrogen" https://www.uofmhealth.org/health-library/aa36271, accessed May 1, 2018.
Bolignano D et al., (2008), 'Neutrophil Gelatinase-Associated Lipocalin (NGAL) as a Marker of Kidney Damage,' Am J Kidney Dis, 52(3):595-605.
Breit SN et al., (2012), 'Macrophage Inhibitory Cytokine-1 (MIC-1/GDF15) and Mortality in End-Stage Renal Disease,' Nephrol Dial Transplant, 27(1):70-5.
Brown DA et al., (2002), 'Concentration in Plasma of Macrophage Inhibitory Cytokine-1 and Risk of Cardiovascular Events in Women: A Nested Case-Control Study,' Lancet, 359(9324):2159-63.
Dübel S et al., 'Chapter 6: Antibody Affinity,' *Handbook of Therapeutic Antibodies*. (1st Ed, 2010), S Dübel and JM Reichert (eds), Wiley-VCH Verlag GmbH, Weinheim, DE (Pub), pp. 119-144 XP007913671.
Heart, (3012), 3(1):20-21, in Japanese with Partial English Translation (4 pages).
Huang JS et al., (2014), 'Klotho Attenuates High Glucose-Induced Fibronectin and Cell Hypertrophy via the ERK1/2-p38 Kinase Signaling Pathway in Renal Interstitial Fibroblasts,' Mol Cell Endocrinol, 390(1-2):45-53.
Gounden et al., (2020) Renal Function Tests, "Blood Urea Nitrogen" [Updated Jun. 20, 2020]. In: StatPearls [Internet]. Treasure Island (FL): StatPearls Publishing; Jan. 2020—. Available from: <https://www.ncbi.nlm.nih.gov/books/NBK507821/>.

(Continued)

*Primary Examiner* — Elizabeth C. Kemmerer
(74) *Attorney, Agent, or Firm* — Dechert LLP; Chad E. Davis

(57) ABSTRACT

The invention provides methods and compositions for treating a subject having a renal-related disorder, such as chronic kidney disease (CKD), end stage renal failure, diabetes, insulin resistance, kidney hypertrophy, kidney hypotrophy, polycystic kidney disease, proteinuria, hyperglycemia, hyperuricemia, gout, kidney stones, hypertension or hypertensive nephropathy, dyslipidemia, anemia and/or reduced erythropoietin production, iron deficiency or hyperfiltration. The methods and compositions use or contain a composition that reduces or inhibits GDF15 activity.

27 Claims, 6 Drawing Sheets

Specification includes a Sequence Listing.

(56) References Cited

OTHER PUBLICATIONS

Inker LA et al., (2012), 'Estimating Glomerular Filtration Rate from Serum Creatinine and Cystatin C,' N Engl J Med, 367(1):20-9.
International Search Report (Form ISA/210) for International Application No. PCT/US2015/036794 dated Nov. 26, 2015 (6 pages).
Jalal Di et al., (2013), 'Uric Acid as a Target of Therapy in CKD,' Am J Kidney Dis, 61 (1):134-46.
Johnen H et al., (2007), 'Tumor-Induced Anorexia and Weight Loss are Mediated by the TGF-62 Superfamily Cytokine MIC-1,' Nat Med, 13(11):1333-40.
Kempf T et al., (2007), 'Prognostic Utility of Growth Differentiation Factor-15 in Patients with Chronic Heart Failure,' J Am Coll Cardiol, 50(11):1054-60.
Kempf T et al., (2011), 'GDF-15 is an Indicator of Leukocyte Integrin Activation Required for Survival and Myocardial Infarction in Mice,' Nat Med, 17(5):581-8.
Krill A et al., (2012), 'Evaluating Compensatory Hypertrophy: A Growth Curve Specific for Solitary Functioning Kidneys,' J Urol, 188(4 Suppl):1613-7.
Larson DS and Coyne DW, (2013), 'Understanding and Exploiting Hepcidin as an Indicator of Anemia due to Chronic Kidney Disease,' Kidney Res Clin Pract, 32(1):11-5.
Levey AS and Coresh J, (2012), 'Chronic Kidney Disease,' Lancet, 379(9811):165-80.
Liabeuf S et al., (2014), 'Clinical Studies and Chronic Kidney Disease: What did we Learn Recently?,' Semin Nephrol, 34(2):164-79.
Lippi G et al., (2011), 'Evaluation of NGAL Test™, a Fully-Automated Neutrophil Gelatinase-Associated Lipocalin (NGAL) Immunoassay on Beckman Coulter AU 5822,' Clin Chem Lab Med, 50(9):1581-4.
Lonberg N, (2008), 'Fully Human Antibodies from Transgenic Mouse and Phage Display Platforms,' Curr Opin Immunol, 20(4):450-9.

Mehta RL et al., (2007), 'Acute Kidney Injury Network: Report of an Initiative to Improve Outcomes in Acute Kidney Injury,' Crit Care, 11(2):R31.
Pons et al., (2017), "Mast Cells and MCPT4 Chymase Promote Renal Impariment after Partial Ureteral Obstructrion," Frontiers in Immunology 8:450, pp. 113.
Roth et al., (2010), "GDF-15 contributes to proliferation and immune escape of malignant gliomas," *Clin Cancer Res.*, 16(15):3851-3859.
Schmitt et al., (2004), "Selectively Reduced Expression of Thick Ascending Limb Tamm-Horsfall Protein in Hypothyroid Kidneys," Histochem. Cell. Biol. 121:319-327.
Seki et al., (2019),"Blood Urea Nitrogen is Independently Associated with Renal Outcomes in Japanese Patients with Stage 3-5 Chronic Kidney Disease: a Prospective Observational Study," *BMC nephrology* vol. 20,1 115, doi:10.1186/s12882-019-1306-1.
Tsai VW-W et al., (2013), 'TGFb Superfamily Cytokine MIC-1/GDF15 is a Physiological Appetite and Body Weight Regulator,' PLOSone, 8(2):e55174 (10 pages).
Wiklund FE et al., (2010), 'Macrophage Inhibitory Cytokine-1 (MIC-1/GDF15): A New Marker of All-Cause Mortality,' Aging Cell, 9(6):1057-64.
Wallentin et al., (2013), "GDF-15 for prognostication of cardiovascular and cancer morbidity and mortality in men," *PloS one*, 8(12), e78797.
Written Opinion of the International Searching Authority for International Application No. PCT/US2015/036794 dated Nov. 26, 2015 (8 pages).
U.S. Appl. No. 15/320,094 Pending, Treatment of Congestive Heart Failure and Other Cardiac Dysfunction Using a GDF15 Modulator, filed Dec. 19, 2016.
U.S. Appl. No. 16/177,792 Pending, Treatment of Congestive Heart Failure and Other Cardiac Dysfunction Using a GDF15 Modulator, filed Nov. 1, 2018.
U.S. Appl. No. 15/320,101 Abandoned, Treatment of Chronic Kidney Disease and other Renal Dysfunction Using a GDF15 Modulator, filed Dec. 19, 2016.

* cited by examiner

SEQUENCE LISTING

```
<160> NUMBER OF SEQ ID NOS: 57

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1
```

```
Asp Tyr Asn Met Asp
1               5

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Thr Tyr Gly Met Gly Val Ser
1               5

<210> SEQ ID NO 3
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Thr Tyr Gly Met Gly Val Gly
1               5

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gln Ile Asn Pro Asn Asn Gly Gly Ile Phe Phe Asn Gln Lys Phe Lys
1               5                   10                  15

Gly

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gln Ile Asn Pro Asn Asn Gly Gly Ile Phe Phe Asn Gln Lys Phe Gln
1               5                   10                  15

Gly

<210> SEQ ID NO 6
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6
```

Gln Ile Asn Pro Tyr Asn His Leu Ile Phe Phe Asn Gln Lys Phe Gln
1               5                   10                  15

Gly

<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gln Ile Asn Pro Asn Asn Gly Leu Ile Phe Phe Asn Gln Lys Phe Gln
1               5                   10                  15

Gly

<210> SEQ ID NO 8
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Ile Asn Pro Asn Asn Gly Leu Ile Phe Phe Asn Gln Lys Phe Lys
1               5                   10                  15

Gly

<210> SEQ ID NO 9
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gln Ile Asn Pro Tyr Asn His Leu Ile Phe Phe Asn Gln Lys Phe Lys
1               5                   10                  15

Gly

<210> SEQ ID NO 10
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

His Ile Tyr Trp Asp Asp Lys Arg Tyr Asn Pro Ser Leu Lys Ser
1               5                   10                  15

<210> SEQ ID NO 11
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic peptide"

<400> SEQUENCE: 11

His Ile Tyr Trp Asp Asp Asp Lys Arg Tyr Asn Pro Ser Leu Lys Thr
1               5                   10                  15

<210> SEQ ID NO 12
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Ile Trp Trp Asp Asp Asp Lys Tyr Tyr Asn Pro Ser Leu Lys Ser
1               5                   10                  15

<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Glu Ala Ile Thr Thr Val Gly Ala Met Asp Tyr
1               5                   10

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Arg Gly Tyr Asp Asp Tyr Trp Gly Tyr
1               5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Arg Gly His Tyr Ser Ala Met Asp Tyr
1               5

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Arg Thr Ser Glu Asn Leu His Asn Tyr Leu Ala
1               5                   10

<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Lys Ala Ser Gln Asn Val Gly Thr Asn Val Ala
1               5                   10

<210> SEQ ID NO 18
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Asp Ala Lys Thr Leu Ala Asp
1               5

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Ala Ser Tyr Arg Tyr Ser
1               5

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Pro Ser Tyr Arg Tyr Ser
1               5

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln His Phe Trp Ser Ser Pro Tyr Thr
1               5

```
<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gln His Phe Trp Ser Asp Pro Tyr Thr
1               5

<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gln Gln Tyr Asn Asn Tyr Pro Leu Thr
1               5

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gln Gln Tyr Asn Ser Tyr Pro His Thr
1               5

<210> SEQ ID NO 25
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Leu His Asn Tyr
            20                  25                  30

Leu Ala Trp Tyr Gln Gln Lys Gln Gly Lys Ser Pro Gln Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125
```

```
Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 26
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Leu His Asn Tyr
            20                  25                  30

Leu Ala Trp Tyr Gln Gln Lys Gln Gly Lys Ser Pro Gln Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 27
<211> LENGTH: 214
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Val
        35                  40                  45

Tyr Asp Ala Lys Thr Leu Ala Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Ile
        35                  40                  45

Tyr Asp Ala Lys Thr Leu Ala Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys Arg Thr Val Ala Ala

```
            100                 105                 110

Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 29
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
                20                  25                  30

Leu Ala Trp Tyr Gln Gln Lys Pro Gly Lys Ala Pro Lys Leu Leu Ile
            35                  40                  45

Tyr Asp Ala Lys Thr Leu Ala Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 30
```

```
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Asp Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Phe Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Ile Leu Thr Ile Ser Asn Val Gln Ser
65                  70                  75                  80
```

```
Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 32
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Phe Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
50                  55                  60

Ser Gly Ser Gly Thr Asp Phe Ile Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 33
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ala Pro Lys Ser Leu Ile
        35                  40                  45

Tyr Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 34
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Pro Ser Tyr Arg Tyr Ser Gly Val Pro Asp Arg Phe Thr Gly
50                  55                  60
```

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro His
            85                  90                  95

Thr Phe Gly Gly Gly Thr Lys Leu Glu Met Lys Arg Ala Asp Ala Ala
        100                 105                 110

Pro Thr Val Ser Ile Phe Pro Pro Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 35
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 35

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Pro Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro His
            85                  90                  95

Thr Phe Gly Gly Gly Thr Lys Leu Glu Met Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 36
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ser Pro Lys Ala Leu Ile
        35                  40                  45

Tyr Ser Pro Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Ser Tyr Pro His
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile

```
        35                  40                  45
Gly Gln Ile Asn Pro Asn Gly Gly Ile Phe Phe Asn Gln Lys Phe
 50                  55                  60
Lys Gly Lys Ala Thr Leu Thr Val Asp Lys Ser Ser Asn Thr Ala Phe
 65                  70                  75                  80
Met Glu Val Arg Ser Leu Thr Ser Glu Asp Thr Ala Val Tyr Tyr Cys
                 85                  90                  95
Ala Arg Glu Ala Ile Thr Thr Val Gly Ala Met Asp Tyr Trp Gly Gln
                100                 105                 110
Gly Thr Ser Val Thr Val Ser Ser Ala Lys Thr Thr Pro Pro Ser Val
                115                 120                 125
Tyr Pro Leu Ala Pro Gly Ser Ala Gln Thr Asn Ser Met Val Thr
 130                 135                 140
Leu Gly Cys Leu Val Lys Gly Tyr Phe Pro Glu Pro Val Thr Val Thr
 145                 150                 155                 160
Trp Asn Ser Gly Ser Leu Ser Ser Gly Val His Thr Phe Pro Ala Val
                165                 170                 175
Leu Gln Ser Asp Leu Tyr Thr Leu Ser Ser Ser Val Thr Val Pro Ser
                180                 185                 190
Ser Thr Trp Pro Ser Glu Thr Val Thr Cys Asn Val Ala His Pro Ala
                195                 200                 205
Ser Ser Thr Lys Val Asp Lys Lys Ile Val Pro Arg Asp Cys Gly Cys
 210                 215                 220
Lys Pro Cys Ile Cys Thr Val Pro Glu Val Ser Ser Val Phe Ile Phe
 225                 230                 235                 240
Pro Pro Lys Pro Lys Asp Val Leu Thr Ile Thr Leu Thr Pro Lys Val
                245                 250                 255
Thr Cys Val Val Val Asp Ile Ser Lys Asp Asp Pro Glu Val Gln Phe
                260                 265                 270
Ser Trp Phe Val Asp Asp Val Glu Val His Thr Ala Gln Thr Gln Pro
                275                 280                 285
Arg Glu Glu Gln Phe Asn Ser Thr Phe Arg Ser Val Ser Glu Leu Pro
 290                 295                 300
Ile Met His Gln Asp Trp Leu Asn Gly Lys Glu Phe Lys Cys Arg Val
 305                 310                 315                 320
Asn Ser Ala Ala Phe Pro Ala Pro Ile Glu Lys Thr Ile Ser Lys Thr
                325                 330                 335
Lys Gly Arg Pro Lys Ala Pro Gln Val Tyr Thr Ile Pro Pro Pro Lys
                340                 345                 350
Glu Gln Met Ala Lys Asp Lys Val Ser Leu Thr Cys Met Ile Thr Asp
                355                 360                 365
Phe Phe Pro Glu Asp Ile Thr Val Glu Trp Gln Trp Asn Gly Gln Pro
 370                 375                 380
Ala Glu Asn Tyr Lys Asn Thr Gln Pro Ile Met Asp Thr Asp Gly Ser
 385                 390                 395                 400
Tyr Phe Val Tyr Ser Lys Leu Asn Val Gln Lys Ser Asn Trp Glu Ala
                405                 410                 415
Gly Asn Thr Phe Thr Cys Ser Val Leu His Glu Gly Leu His Asn His
                420                 425                 430
His Thr Glu Lys Ser Leu Ser His Ser Pro Gly Lys
                435                 440

<210> SEQ ID NO 38
```

<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

```
Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Lys Ala Thr Leu Thr Val Asp Lys Ser Ser Asn Thr Ala Phe
65                  70                  75                  80

Met Glu Val Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 39
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Asn Met Asp Trp Val Arg Gln Ala Pro Gly Lys Ser Leu Glu Trp Ile
        35                  40                  45
Gly Gln Ile Asn Pro Asn Asn Gly Gly Ile Phe Phe Asn Gln Lys Phe
    50                  55                  60
Lys Gly Arg Ala Thr Leu Thr Val Asp Thr Ser Thr Asn Thr Ala Tyr
65                  70                  75                  80
Met Glu Leu Arg Ser Leu Arg Ser Asp Asp Thr Ala Val Tyr Tyr Cys
                85                  90                  95
Ala Arg Glu Ala Ile Thr Thr Val Gly Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
```

```
                    260                 265                 270
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 40
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Arg Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 41
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45
```

```
Gly Gln Ile Asn Pro Asn Asn Gly Gly Ile Phe Phe Asn Gln Lys Phe
    50                  55                  60

Lys Gly Arg Val Thr Leu Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 42
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 43
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

-continued

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 44
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser

```
            145                 150                 155                 160
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 45
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
                20                  25                  30

Asn Met Asp Trp Val Arg Gln Ala Pro Gly Gln Gly Leu Glu Trp Met
                35                  40                  45
```

```
Gly Gln Ile Asn Pro Asn Asn Gly Gly Ile Phe Phe Asn Gln Lys Phe
    50                  55                  60
Gln Gly Arg Val Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Ala Ile Thr Thr Val Gly Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450
```

<210> SEQ ID NO 46
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Tyr Asn His Leu Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

-continued

```
                355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 47
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
                20                  25                  30
Asn Met Asp Trp Val Arg Gln Ala Pro Gly Gln Ser Leu Glu Trp Met
            35                  40                  45
Gly Gln Ile Asn Pro Asn Asn Gly Leu Ile Phe Phe Asn Gln Lys Phe
        50                  55                  60
Gln Gly Arg Val Thr Leu Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Glu Ala Ile Thr Thr Val Gly Ala Met Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
            195                 200                 205
Pro Ser Asn Thr Lys Val Asp Lys Arg Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 48
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Leu Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 49
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met

```
            35                  40                  45
Gly Gln Ile Asn Pro Tyr Asn His Leu Ile Phe Phe Asn Gln Lys Phe
 50                  55                  60

Lys Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ala Ile Thr Thr Val Gly Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450
```

<210> SEQ ID NO 50
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Ala Ser Asn Asn Arg Val
65              70                  75                  80

Phe Leu Lys Ile Thr Ser Val Asp Thr Ala Asp Thr Ala Thr Tyr Tyr
            85                  90                  95

Cys Ala Gln Arg Gly Tyr Asp Asp Tyr Trp Gly Tyr Trp Gly Gln Gly
        100                 105                 110

Thr Leu Val Thr Ile Ser Ala Ala Lys Thr Thr Pro Pro Ser Val Tyr
    115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Ser Val Thr Val Pro Ser Ser
        180                 185                 190

Thr Trp Pro Ser Glu Thr Val Thr Cys Asn Val Ala His Pro Ala Ser
    195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
            245                 250                 255

Cys Val Val Val Asp Ile Ser Lys Asp Asp Pro Glu Val Gln Phe Ser
        260                 265                 270

Trp Phe Val Asp Asp Val Glu Val His Thr Ala Gln Thr Gln Pro Arg
    275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
            325                 330                 335

Gly Arg Pro Lys Ala Pro Gln Val Tyr Thr Ile Pro Pro Lys Glu
        340                 345                 350

```
Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440
```

<210> SEQ ID NO 51
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
50                  55                  60

Leu Lys Thr Arg Leu Thr Ile Ser Lys Asp Thr Ser Lys Asn Gln Val
65                  70                  75                  80

Val Leu Thr Ile Thr Asn Val Asp Pro Val Asp Thr Ala Val Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
                260             265             270
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 52
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 53
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asp Ile Trp Trp Asp Asp Lys Tyr Tyr Asn Pro Ser
    50                  55                  60
```

```
Leu Lys Ser Arg Leu Thr Ile Ser Lys Asp Thr Ser Asn Glu Val
 65                  70                  75                  80

Phe Leu Lys Ile Ala Ile Val Asp Thr Ala Asp Thr Ala Thr Tyr Tyr
                 85                  90                  95

Cys Ala Arg Arg Gly His Tyr Ser Ala Met Asp Tyr Trp Gly Gln Gly
                100                 105                 110

Thr Ser Val Thr Val Ser Ser Ala Lys Thr Thr Pro Pro Ser Val Tyr
                115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
                180                 185                 190

Thr Trp Pro Ser Glu Thr Val Thr Cys Asn Val Ala His Pro Ala Ser
                195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
                275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
                355                 360                 365

Phe Pro Glu Asp Ile Thr Val Glu Trp Gln Trp Asn Gly Gln Pro Ala
                370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
                435                 440
```

<210> SEQ ID NO 54
<211> LENGTH: 449
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 54

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asp Ile Trp Trp Asp Asp Lys Tyr Tyr Asn Pro Ser
50                  55                  60

Leu Lys Ser Arg Leu Thr Ile Ser Lys Asp Thr Ser Ser Asn Glu Val
65                  70                  75                  80

Phe Leu Lys Ile Ala Ile Val Asp Thr Ala Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
```

```
                385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 55
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Ala Ser Asn Asn Arg Val
65                  70                  75                  80

Phe Leu Lys Ile Thr Ser Val Asp Thr Ala Asp Thr Ala Thr Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 56
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

-continued

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 57
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95

-continued

```
Cys Ala Arg Arg Gly His Tyr Ser Ala Met Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

TREATMENT OF CHRONIC KIDNEY DISEASE AND OTHER RENAL DYSFUNCTION USING A GDF15 MODULATOR

CROSS-REFERENCE TO RELATED APPLICATIONS

This application is a continuation of U.S. patent application Ser. No. 15/320,101, filed Dec. 19, 2016, now abandoned, which is a national stage application filed under 35 U.S.C. § 371 of International Patent Application No. PCT/US2015/036794, filed Jun. 19, 2015, which claims priority to and the benefit of U.S. Provisional Patent Application No. 62/015,242, filed Jun. 20, 2014, the contents of each of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Nov. 2, 2018, is named Sequence_Listing_filed_1102.txt and is 114,714 bytes in size.

FIELD OF THE INVENTION

The present invention relates to methods of using, and compositions containing, a GDF15 modulator for treating a subject having a renal disorder or renal dysfunction, particularly chronic kidney disease, acute, chronic or end stage renal failure, glomerulonephritis, anemia, diabetic nephropathy and insulin resistance.

BACKGROUND OF THE INVENTION

Kidney disease is a common and expensive condition that is a major source of morbidity and mortality in humans. From a clinical perspective, kidney diseases can be classified as acute kidney injury (AKI) and chronic kidney disease (CKD). AKI, also termed acute kidney failure or acute renal failure, is a rapid loss of renal function, and may end up with full, partial or no recovery of normal renal function. AKI is an abrupt (within 48 hours) reduction in kidney function, which may include an absolute increase in serum creatinine of at least 0.3 mg/dl, a percentage increase in serum creatinine of at least 50%, or a reduction in urine output of less than 0.5 ml/kg per hour for more than six hours. See Metha et al., 2007, CRITICAL CARE, 11: R31. Epidemiologically, AKI may be brought about post-renally, through obstruction of the urinary collection system by either intrinsic or extrinsic masses. Alternatively, AKI may originate within the renal system itself, by disorders of or injury affecting the structures of the nephron, such as the glomeruli, tubules, vessels, or interstitium.

CKD is a progressive loss of function over a prolonged period of time. An AKI patient who does not recover renal function may progress to CKD. Moreover, CKD-affected patients are prone to suffer AKI-like events.

Growth Differentiation Factor-15 (GDF15) is a member of the transforming growth factor-beta (TGF-β) superfamily of proteins, which comprise a large group of multifunctional proteins that serve as regulators of cell proliferation and differentiation. Prominent members of this family include the TGF-βs 1-5, activins, bone morphogenetic proteins (BMPs) that serve as regulators of bone, cartilage and other tissue types, and other proteins involved in cellular regulation, such as glial cell-line derived neurotrophic factor (GDNF), and myostatin (also known as GDF-8). GDF15 was initially isolated from tissues such as prostate and placenta, and has been known by the additional names macrophage inhibitory cytokine 1 (or MIC1), NSAID-activated gene 1 protein (or NAG1), NSAID-regulated gene 1 protein (or NRG-1), placental TGF-beta (or PTGFB), placental bone morphogenetic protein (or PLAB), and prostate differentiation factor (or PDF).

Notwithstanding the progress made to date, there still exists a need for new methods and compositions for detecting, preventing and/or treating renal conditions and disorders, such as acute kidney injury and chronic kidney disease.

SUMMARY OF THE INVENTION

The present invention provides methods and compositions useful for detecting, preventing, and treating conditions and disorders that involve disease, dysfunction, hypertrophy or hypotrophy of kidneys or renal tissue. Such conditions include, for example, chronic kidney or end stage renal failure, uremic syndrome, anemia and/or reduced erythropoietin production from the kidneys, diabetes, insulin resistance and reduced kidney function or kidney size.

The present inventors have discovered that, among other things, subjects suffering from renal conditions and disorders, such as chronic kidney disease, that are not effectively or optimally treated with presently available methods may be effectively treated with a composition that selectively reduces or inhibits GDF15 activity. The invention comprises compositions which reduce or inhibit the activity of GDF15, for example, by reducing the ability of GDF15 to bind to an endogenous binding partner (also referred to as cognate receptor or binding partner), for example, by competitively binding to GDF15 or to an endogenous binding partner, or by otherwise neutralizing the activity of GDF15. In certain embodiments, such a composition may comprise an antibody that binds to GDF15 or an endogenous binding partner, as well as a peptide or fusion molecule that comprises such an antibody. In certain other embodiments, the composition may comprise a peptide or small molecule that binds, for example, competitively binds, to GDF15 or to an endogenous binding partner, such that the activity of GDF15 is reduced or inhibited, for example, by reducing or inhibiting the ability of GDF15 to bind to its endogenous binding partner or otherwise neutralizing the activity of GDF15.

In one aspect, the invention provides a method of increasing renal function in a subject in need thereof, the method comprising administering an effective amount of a composition comprising a GDF15 modulator thereby to increase renal function in the subject. Renal function can include any of the biochemical and physiological parameters discussed below.

In another aspect, the invention provides a method of treating a subject having a renal disorder or renal dysfunction, the method comprising administering an effective amount of a composition comprising a GDF15 modulator thereby to ameliorate a symptom of the renal disorder or renal dysfunction. The symptoms can include any of the biochemical and physiological parameters discussed below.

In another aspect, the invention provides a method of reducing or reversing renal hypotrophy in a subject in need thereof wherein the subject has one or more symptoms of chronic kidney disease, the method comprising administering an effective amount of a composition comprising a GDF15 modulator thereby to reduce or reverse renal hypotrophy in the subject. The symptoms can include any of the biochemical and physiological parameters discussed below.

In another aspect, the invention provides a method of treating or preventing chronic kidney disease (CKD) in a subject in need thereof, the method comprising administering to the subject an effective amount of a composition comprising a GDF15 modulator thereby to treat or prevent CKD in the subject.

In certain embodiments, the subject exhibits a glomerular filtration rate (GFR) below 90 ml creatinine/minute/1.73 m$^2$ body-surface area. In certain embodiments, the subject exhibits albuminuria (e.g., urinary excretion of albumin in excess of 30 mg per day, 30 mg per liter of urine, or 30 μg/mg of creatinine in urine). In certain embodiments, the subject exhibits hyperuricemia, exhibits a serum uric acid level of at least 6.3 mg/dL, exhibits iron deficiency, or exhibits transferrin saturation of below 25% and a low ferritin level. In certain embodiments, the subject has been diagnosed as having chronic kidney disease.

In certain embodiments, the GDF15 modulator of the invention can decrease or inhibit GDF15 activity in the subject. In certain embodiments, the GDF15 modulator inhibits the activity, expression or binding of GDF15 to its cognate receptor. The GDF15 modulator can be an anti-GDF15 antibody, which can be humanized or human.

In other embodiments, the invention comprises a method of treating a subject exhibiting one or more of the following characteristics, which can be indicative of renal dysfunction or disease, such as chronic kidney disease. Such renal-related characteristics include:

(1) the subject exhibits reduced or below normal glomerular filtration rate (GFR);
(2) the subject exhibits albuminuria (microalbuminuria or macroalbuminuria);
(3) the subject exhibits elevated or above normal levels of serum creatinine (SCr);
(4) the subject exhibits reduced or below normal levels of urine output;
(5) the subject exhibits increased or above normal urinary excretion of neutrophil gelatinase-associated lipocalin (NGAL);
(6) the subject exhibits signs of proteinuria (protein in the urine), such as albumin, 2 macroglobulin or IgG, in amounts greater than 3.5 g/day;
(7) the subject exhibits hyperglycemia, hyperuricemia or dyslipidemia;
(8) the subject exhibits anemia or reduced erythropoietin production;
(9) the subject exhibits iron deficiency;
(10) the subject exhibits hyperfiltration;
(11) the subject has experienced, or is diagnosed to be at risk of experiencing a kidney failure;
(12) the subject has had, or has been diagnosed as being in need of, renal intervention, such as a kidney transplant or dialysis;
(13) the subject exhibits renal hypertrophy or renal hypotrophy;
(14) the subject exhibits levels of one or more biomarkers that are indicative of renal dysfunction.

In certain embodiments, useful biomarkers indicative of renal dysfunction include one or more of the following: cystatin C in the urine or plasma; urinary C-reactive protein (uCRP); urinary retinol-binding protein (uRBP); neutrophil gelatinase-associated lipocalin (NGAL); hepcidin; creatinine; hemojuvelin; uric acid and/or urea; beta trace protein; kidney injury molecule-1 (KIM-1); urinary N-acetyl-beta-(D)-glucosaminidase (NAG); urinary interleukin-18 (uIL-18); liver fatty acid binding protein-1 (L-FABP-1); blood urea nitrogen (BUN); micro-RNA 21 (miRNA-21); and electrolytes.

Subjects with abnormal levels of these biomarkers may be candidates for treatment with GDF15 modulators. In some embodiments, the clinician will use one or more of the above characteristics in combination with other observations, such as family history of kidney disease, or whether the subject has had, or has been diagnosed as requiring renal intervention, such as kidney transplant or dialysis.

The above renal-related characteristics and biomarkers can also be used to monitor the subject's progress in response to treatment with a GDF15 modulator in accordance with the present invention, and to modify the dosing regimen if deemed clinically appropriate. In certain embodiments, the subject having a renal disorder, such as chronic kidney disease (CKD), has previously been treated with a known renal treatment, such as dialysis, but persists in exhibiting at least one of the above characteristics. In such cases, the present invention provides methods and compositions for avoiding or reducing the occurrence and/or severity of at least one of the above renal-related characteristics, and may also avoid or reduce the need for further renal treatments, by administering to the subject a GDF15 inhibitor.

In yet another aspect, the present invention comprises methods of improving at least one of the following characteristics in a subject, wherein the subject has been diagnosed as, or considered to be at risk of developing chronic kidney disease:

(1) reduced or below normal glomerular filtration rate (GFR);
(2) elevated or above normal levels of serum creatinine (SCr);
(3) reduced or below normal levels of urine output;
(4) increased or above normal urinary excretion of neutrophil gelatinase-associated lipocalin (NGAL);
(5) signs of proteinuria (protein in the urine), such as albumin, 2-macroglobulin or IgG, in amounts greater than 3.5 g/day;
(6) hyperglycemia, hyperuricemia or dyslipidemia;
(7) anemia or reduced erythropoietin production;
(8) iron deficiency;
(9) hyperfiltration; or
(10) has experienced, or is diagnosed to be at risk of experiencing a kidney failure;
(11) has had, or has been diagnosed as being in need of, renal intervention, such as a kidney transplant or dialysis.
(12) renal hypertrophy or renal hypotrophy;
(13) levels of one or more biomarkers that are indicative of renal dysfunction.

In certain embodiments, the GDF15 modulator of the invention can decrease or inhibit GDF15 activity in the subject. In certain embodiments, the GDF15 modulator inhibits the activity, expression or binding of GDF15 to its cognate receptor. The GDF15 modulator can be an anti-GDF15 antibody, which can be humanized or human.

The above renal-related characteristics can be monitored to confirm the subject's progress in response to treatment with GDF15 binding inhibitors in accordance with the present invention, and to modify the dosage regime if deemed clinically appropriate. In certain embodiments, the subject having a renal disorder, such as chronic kidney disease (CKD), has previously been treated with a known renal treatment, but persists in exhibiting at least one of the above characteristics. In such cases, the present invention provides methods and compositions for avoiding or reducing the occurrence and/or severity of at least one of the above characteristics, and may also avoid or reduce the need for one of the renal interventions described above.

DETAILED DESCRIPTION OF THE INVENTION

Figure 1:
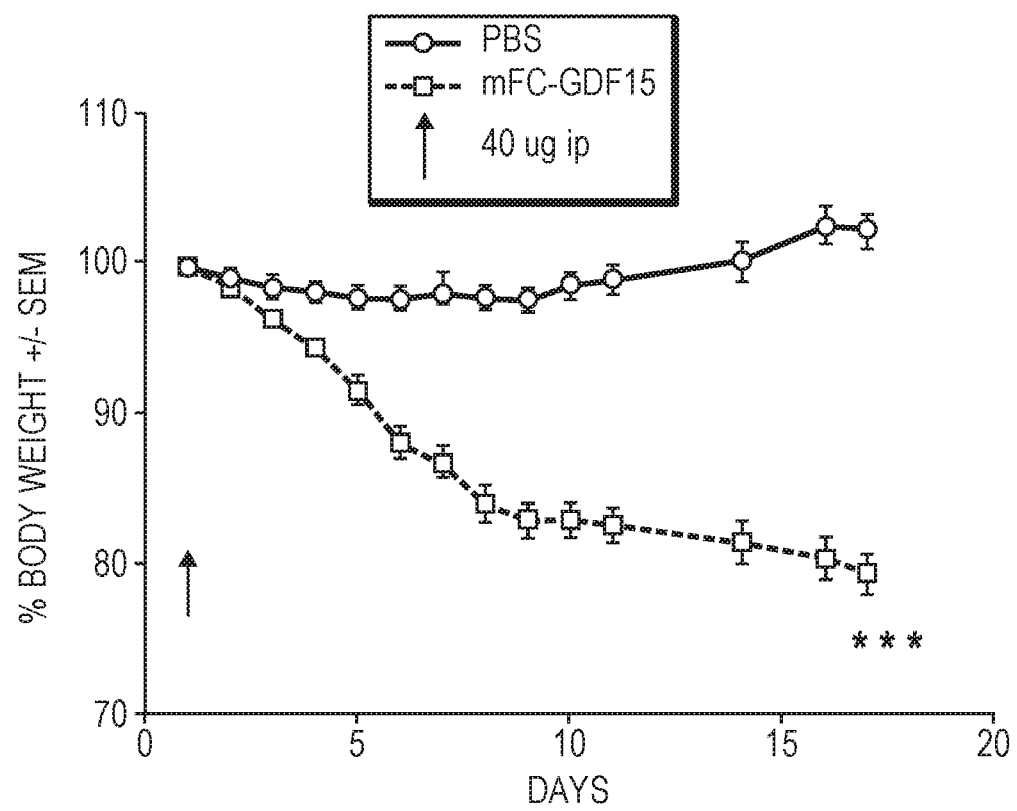
FIG. 1 is a graph showing the effect on mice of intra-peritoneal administration of 40 µg recombinant murine Fc-GDF15 protein or phosphate buffered saline (PBS), where body weight decreased significantly in animals treated with mFC-GDF15 (■) but not with PBS (●).

The present invention provides methods and compositions for treating a subject having any of a number of kidney-related or renal disease states, for example, a subject having chronic kidney disease, end stage renal failure, diabetes, insulin resistance, kidney hypertrophy, kidney hypotrophy, polycystic kidney disease, proteinuria, hyperglycemia, hyperuricemia, uremic syndrome, gout, kidney stones, hypertension or hypertensive nephropathy, dyslipidemia, anemia and/or reduced erythropoietin production; iron deficiency or hyperfiltration, where such disease state is associated with a renal disorder. The methods and compositions may be useful in treating a subject with chronic kidney disease, which may be caused by the above disease states, or who exhibits at least one characteristic that is symptomatic of chronic kidney disease, renal failure, uremic syndrome, renal dystrophies, other renal conditions or disorders, acute kidney injury, acute kidney disease or adverse clinical outcomes resulting in acute renal failure, for example, obstructive nephropathy, including one or more of the following:

(1) reduced or below normal glomerular filtration rate (GFR);
(2) elevated or above normal levels of serum creatinine (SCr);
(3) reduced or below normal levels of urine output;
(4) increased or above normal urinary excretion of neutrophil gelatinase-associated lipocalin (NGAL);
(5) signs of proteinuria (protein in the urine), such as albumin, 2 macroglobulin or IgG, in amounts greater than 3.5 g/day;
(6) hyperglycemia, hyperuricemia or dyslipidemia;
(7) anemia or reduced erythropoietin production;
(8) iron deficiency;
(9) hyperfiltration; or
(10) is experiencing, or is diagnosed to be at risk of experiencing a kidney failure;
(11) has had, or has been diagnosed as needing renal intervention, such as a kidney transplant or dialysis.
(12) renal hypertrophy or renal hypotrophy;
(13) levels of one or more biomarkers that are indicative of renal dysfunction.

In a particular embodiment of the present invention, the subject exhibits chronic kidney disease (CKD). Accordingly, a subject having CKD or another kidney-related disease or disorder who exhibits symptoms of CKD or who is diagnosed as having CKD or at risk of having CKD may not be optimally treated by existing treatments. In such cases, treatment in accordance with the methods and compositions of the present invention may be especially beneficial in improving one or more of the characteristics above. In particular embodiments, the subject exhibits one or more of the following characteristics such that the subject is considered to have CKD or considered to be suffering from CKD, such that the subject may benefit from treatment according to the present invention. As used throughout the application, the term "considered to have CKD" or "considered to be suffering from CKD" means that following the disclosure of this application, one skilled in the art would expect that a subject would benefit from the administration of GDF15 inhibitors in accordance with the present invention. A subject is also "considered to have CKD" or "considered to be suffering from CKD" if a qualified clinical professional, after examination of information related to the subject, has made the professional judgment or diagnosis that the subject presently suffers from CKD. The term "considered to be at risk of developing CKD" means that, following the disclosure of this application, one skilled in the art would expect that a subject would benefit from the prophylactic or therapeutic administration of GDF15 inhibitors in accordance with the present invention. A subject is also term "considered to be at risk of developing CKD" if a qualified clinical professional, after examination of information related to the subject, has made the professional judgment or diagnosis that the subject presently a risk of developing CKD, sufficient to justify prophylactic or therapeutic intervention.

As used herein, "treat," "treating" and "treatment" mean the treatment of a disease in a mammal, e.g., in a human. This includes: (a) inhibiting the disease, i.e., arresting its development; and (b) relieving the disease, i.e., causing regression of the disease state.

I. Symptoms of Chronic Kidney Disease, Renal Failure or Kidney Dysfunction

A major criteria useful for the classification, diagnosis and monitoring of subjects for chronic kidney disease is glomerular filtration rate (GFR). The National Kidney Foundation has established criteria for the definition of CKD in which a subject with one or more CKD risk factors. Generally, GFR is measured in terms of clearance or filtration of ml of creatinine per minute per 1.73 m$^2$ body-surface area. However, cystatin C, another marker for CKD prognosis, is a potential alternative to serum creatinine for estimating GFR. See, Inker et al., 2012, N. E. J. MEDICINE, 367:20-29.

A subject exhibiting GFR less than 90 is considered to have CKD. A subject exhibiting GFR greater than or equal to 90 (ml/minute/1.73 m$^2$ body-surface area) may be considered to be at CKD stage 1, or at an increased risk of CKD, after taking into consideration other indicators of CKD. For example, indicators of CKD risk factors include higher than normal levels of creatinine or urea in the blood, blood or protein in the urine, and a family history of polycystic kidney disease. A subject exhibiting kidney damage with a GFR between 60 and 89 ml/minute/1.73 m$^2$ body-surface area is considered to be at CKD stage 2. A subject exhibiting a GFR between 30 and 59 ml/minute/1.73 m$^2$ body-surface area is considered to be at CKD stage 3, at which many clinicians consider the possibilities of renal intervention. Among the interventions are strict dietary modification plans, in which daily intake of phosphorus, calcium, carbohydrates and sodium may be recommended. Supplementation of the diet with protein, water-soluble vitamin B complex, and vitamin C also may be recommended. A subject exhibiting GFR between 15 and 29 ml/minute/1.73 m$^2$ body-surface area is considered to be at CKD stage 4, at which many clinicians consider dialysis and/or preparation for kidney replacement. A subject exhibiting GFR of less than 15 ml/minute/1.73 m$^2$ body-surface area is considered to be at CKD stage 5, or kidney failure, an urgent stage at which intervention such as kidney replacement may be urgently needed, particularly if uremia is present. A subject presenting with CKD stages 1-5 may benefit from therapy according to the present invention, in order to fully or partially restore the loss of kidney function, or to slow or prevent further deterioration of kidney function.

A subject is considered to be suffering from chronic kidney disease if their urinary NGAL levels are in excess 50 μg/L; and more serious CKD if the urinary or plasmatic NGAL levels are in excess of 100 μg/L. Lippi et al., 2011, CLIN CHEM LAB MED, 50(9):1581-1584; Bolignano et al., 2008, AMERICAN J. OF KIDNEY DISEASES, 52:595-605.

A subject can be considered to be suffering from chronic kidney disease if they exhibit microalbuminuria: urinary excretion of albumin in excess of 30 mg per day, 30 mg per liter of urine, or 30 μg/mg of creatinine in urine. A subject is considered to be suffering from serious CKD if they exhibit macroalbuminuria: their urinary excretion of albumin is 300 mg or more per day, 300 mg or more per liter of urine, or 300 μg or more/mg of creatinine in urine. See Levey and Coresh, 2012, THE LANCET, 379:165-180.

For purposes of the present invention, a subject is considered to be suffering from chronic kidney disease if they exhibit uric acid in the blood in excess of 530 micromol/L (6 mg/dL) for women and 619 micromol/L (7 mg/dL) for men or if they suffer from kidney stones. See also, peak VO$_2$, Jalal et al., 2012, AM. J. OF KIDNEY DISEASE, 62:134-146.

For purposes of the present invention, a subject is considered to be suffering from chronic kidney disease if they exhibit iron deficiency, particularly a low transferrin saturation (<25%) coupled with low ferritin (<200 ng/mL in dialysis patients; <100 ng/mL in non-dialysis patients). See Larson and Coyne, 2013, KIDNEY RESEARCH AND CLINICAL PRACTICE, 32:11-15.

For purposes of the present invention, a subject is considered to be suffering from chronic kidney disease if they experience renal or kidney hypertrophy, hyperplasia, or increase in kidney mass, which is due to underlying disease. Kidney hypertrophy may be compensatory, for loss of kidney tissue function. For example, hypertrophy is frequently observed in patients with a solitary functional kidney. Krill et al., 2012, J. UROLOGY, 188 supp: 1613-1617. Cell hypertrophy can be assessed by total protein/cell and electronic volume. See Huang et al., 2014, MOLECULAR AND CELLULAR ENDOCRINOLOGY, 390:45-53.

For purposes of the present invention, a subject is considered to be suffering from chronic kidney disease if they experience renal hypotrophy, hypoplasia, or significant decrease in kidney mass. Renal hypotrophy can be assessed, for example, by magnetic resonance imaging. See Chang et al., 2007, J. UROLOGY, 178:2550-2554.

In particular embodiments of the present invention, the subject exhibits one or more additional symptoms of chronic kidney disease. This may include one or more of the following indicators of chronic kidney disease, renal failure or kidney dysfunction: increased serum creatinine levels, decreased serum bilirubin levels, increased urine albumin concentration, increased urinary creatinine levels, increased urinary albumin-to-creatine ratio (albumin-to-creatinine ratio of 25 mg/g or higher in women and 17 mg/g or higher in men, with a value of 30 mg/g indicative of serious CKD), increased urinary protein-to-creatinine ratio (protein-to-creatinine ratio of 200 mg/g is considered to be too high and indicative of CKD), hypertension (defined as systolic blood pressure of 140 mm Hg or above; diastolic blood pressure of 90 mm Hg or above; or undergoing current antihypertensive drug treatment), diabetes mellitus (defined as fasting glucose level of 126 mg/dL or higher; or the use of insulin or oral hypoglycemic medications); appearance of cystatin C in the urine or plasma, urinary C-reactive protein (uCRP), urinary retinol-binding protein (uRBP), hepcidin, increased serum levels of creatinine, hemojuvelin; uric acid and/or urea; beta trace protein; kidney injury molecule-1 (KIM-1); urinary N-acetyl-beta-(D)-glucosaminidase (NAG); urinary interleukin-18 (uIL-18); liver fatty acid binding protein-1 (L-FABP-1); blood urea nitrogen (BUN); micro-RNA 21 (miRNA-21); and electrolytes.

In certain embodiments, useful biomarkers indicative of renal dysfunction include one or more of the following: cystatin C in the urine or plasma; urinary C-reactive protein (uCRP); urinary retinol-binding protein (uRBP); neutrophil gelatinase-associated lipocalin (NGAL); hepcidin; creatinine; hemojuvelin; uric acid and/or urea; beta trace protein; kidney injury molecule-1 (KIM-1); urinary N-acetyl-beta-(D)-glucosaminidase (NAG); urinary interleukin-18 (uIL-18); liver fatty acid binding protein-1 (L-FABP-1); blood urea nitrogen (BUN); micro-RNA 21 (miRNA-21); and electrolytes.

In addition, retention of potentially toxic solutes, including phosphates, dimethyarginines (asymmetric, or ADMA, and symmetric, or SDMA), uric acid, parathyroid hormone (PTH), fibroblast growth factor 23 (FGF23), beta-2 microalbumin (B2M), interleukin-6 (IL-6), protein-bound indoxyl sulfate (IS) and p-cresol and its conjugates, p-cresylsulfate (PCS) and p-cresylglucuronide (PCG), may be indicative of decreased renal function or a renal disorder, e.g., "uremic syndrome." See, Liabeuf et al., 2014, SEMIN NEPHROL, 34(2): 164-179, http://dx.doi.org/10.1016/j.semnephro.2014.02.008.

Subjects with abnormal levels of these biomarkers may be candidates for treatment with GDF15 modulators. In some embodiments, the clinician will use one or more of the above characteristics in combination with other observations, such as family history of kidney disease, or whether the subject has had, or has been diagnosed as requiring renal intervention, such as kidney transplant or dialysis.

The above renal-related characteristics and biomarkers can also be used to monitor the subject's progress in response to treatment with a GDF15 modulator in accordance with the present invention, and to modify the dosing regimen if deemed clinically appropriate. In certain embodiments, the subject having a renal disorder, such as chronic kidney disease (CKD), has previously been treated with a known renal treatment, such as dialysis, but persists in exhibiting at least one of the above characteristics. In such cases, the present invention provides methods and compositions for avoiding or reducing the occurrence and/or severity of at least one of the above renal-related characteristics, and may also avoid or reduce the need for further renal treatments, by administering to the subject a GDF15 inhibitor.

In addition to each of the foregoing, the subject may also exhibit elevated levels of GDF15 activity relative to a baseline activity level present in subjects without the renal disorder or dysfunction.

Elevated levels of GDF15 activity can determined by measuring the level of GDF15 in a sample from a subject. The amount regarded as an "elevated level" of GDF15 may vary according to the particular tissue or body fluid of interest, as well as the particular assay that is utilized. Generally, an "elevated level" of GDF15 may be determined relative to a control distribution of subjects, for example, subjects without a renal disease or dysfunction, for example, CKD, and may be determined at a pre-specified cutoff of, for example, the $75^{th}$ percentile (i.e., upper quartile or 25%); $90^{th}$ percentile (i.e., upper 10%); or $95^{th}$ percentile (i.e., upper 5%). An "elevated level" of GDF15 may also be determined at a pre-specified GDF15 level above the mean, for example one standard deviation above the mean, or two standard deviations above the mean average GDF15 level of a group of control subjects without renal disease or dysfunction, for example, CKD. See, for example, Brown et al., 2002, THE LANCET 359:2159-2163; Kempf et al., 2011, NATURE MEDICINE, 17:581-588.

The preferred body sample is a body fluid, for example, a sample of blood plasma, however a sample of amniotic fluid, placental extract, whole blood, serum, buffy coat, urine, cerebrospinal fluid, seminal fluid, synovial fluid, or a tissue biopsy may also be suitable. A GDF15 concentration of >600 pg/ml, optionally >850 pg/ml, optionally >1000 pg/ml, optionally >1200 pg/ml, optionally >1500 pg/ml, optionally >1700 pg/ml, optionally >1900 pg/ml, optionally >2000 pg/ml, optionally >2500 pg/ml, and optionally >3000 pg/ml in a body fluid, for example, plasma can represent an elevated level of GDF15. See, U.S. Pat. No. 7,919,084 and Kempf et al., 2007, J. AM. COLL. CARDIOL. 50:1054-1060.

The amount of GDF15 present in a body sample may be readily determined by, for example, immunoassays (e.g., with a body fluid) or immunohistochemistry (e.g., with sectionalized samples of a tissue biopsy) using an anti-GDF15 antibody. See Tsai et al., 2013, PLOS ONE, 8: e55174.

II. Comorbidities of Chronic Kidney Disease

Chronic kidney disease is frequently complicated by the occurrence of comorbidities, which may range from minor to serious in degree. It is an advantage of the present invention that inhibition of GDF15 may additionally assist in reducing one or more common comorbidities of CKD. Among the frequent comorbidities of CKD are cachexia, chronic or congestive heart failure, anemia, diabetes and hypertension. Accordingly, the present invention includes methods of increasing renal function in a subject in need thereof, the method comprising administering an effective amount of a composition comprising a GDF15 inhibitor to increase renal function in a subject who. For example, the subject suffering from renal dysfunction or CKD may exhibit a comorbidity of cachexia, chronic or congestive heart failure, anemia, diabetes or hypertension.

III. GDF15 Modulators

As used herein a "GDF15 modulator" is understood to mean an agent that reduces or inhibits GDF15 activity, which can result from reduced expression, amount, or biological activity or function, of GDF15. GDF15 modulators or modulating agents useful in the practice of the invention may comprise an anti-GDF15 antibody, an anti-GDF15 receptor antibody, soluble GDF15 mimetics or analogs that prevent GDF15 from binding to its cognate binding partner, a soluble GDF15 receptor mimetic or analog that prevents GDF15 from binding to its cognate binding partner. Additional exemplary GDF15 modulating agents include small molecule inhibitors of GDF15 or a GDF15 receptor, interfering nucleic acids (for example, interfering RNA or antisense nucleic acids (for example, antisense DNA or RNA) that interfere with expression of endogenous GDF15 or a cognate receptor.

In a preferred embodiment, the GDF15 modulating agent can comprise an anti-GDF15 antibody, which is humanized or human. As used herein, unless otherwise indicated, the term "antibody" is understood to mean an intact antibody (e.g., an intact monoclonal antibody) or antigen-binding fragment of an antibody, including an intact antibody or antigen-binding fragment of an antibody (e.g., a phage display antibody including a fully human antibody, a semi-synthetic antibody or a fully synthetic antibody) that has been optimized, engineered or chemically conjugated. Examples of antibodies that have been optimized are affinity-matured antibodies. Examples of antibodies that have been engineered are Fc optimized antibodies, and multispecific antibodies (e.g., bispecific antibodies). Examples of antigen-binding fragments include Fab, Fab', F(ab')$_2$, Fv, single chain antibodies (e.g., scFv), minibodies and diabodies. An antibody conjugated to a toxin moiety is an example of a chemically conjugated antibody.

In certain embodiments, the antibody comprises: (a) an immunoglobulin heavy chain variable region comprising the structure $CDR_{H1}$-$CDR_{H2}$-$CDR_{H3}$ and (b) an immunoglobulin light chain variable region, wherein the heavy chain variable region and the light chain variable region together define a single binding site for binding GDF15 or a GDF15 receptor. The $CDR_{H1}$, $CDR_{H2}$, and $CDR_{H3}$ sequences are interposed between immunoglobulin framework (FR) sequences. In certain other embodiments, the antibody comprises (a) an immunoglobulin light chain variable region comprising the structure $CDR_{L1}$-$CDR_{L2}$-$CDR_{L3}$, and (b) an immunoglobulin heavy chain variable region, wherein the IgG light chain variable region and the IgG heavy chain variable region together define a single binding site for binding GDF15 or a GDF15 receptor. The $CDR_{L1}$, $CDR_{L2}$, and $CDR_{L3}$ sequences are interposed between immunoglobulin FR sequences. In certain other embodiments, the antibody comprises: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding GDF15 or a GDF15 receptor. Exemplary anti-GDF15 antibodies are described, for example, in U.S. Patent Publication No. US 2014-0193427-A1, the disclosure of which is incorporated by reference herein for all purposes.

Exemplary anti-GDF15 antibodies useful in the methods and compositions of the invention may, for example, include a heavy chain variable region comprising any one of the nine sets of $CDR_{H1}$, $CDR_{H2}$, and $CDR_{H3}$ region sequences set forth in Table 1 below.

TABLE 1

| | $CDR_{H1}$ | $CDR_{H2}$ | $CDR_{H3}$ |
|---|---|---|---|
| 1 | DYNMD (SEQ ID NO: 1) | QINPNNGGIFFNQKFKG (SEQ ID NO: 4) | EAITTVGAMDY (SEQ ID NO: 13) |
| 2 | DYNMD (SEQ ID NO: 1) | QINPNNGGIFFNQKFQG (SEQ ID NO: 5) | EAITTVGAMDY (SEQ ID NO: 13) |
| 3 | DYNMD (SEQ ID NO: 1) | QINPYNHLIFFNQKFQG (SEQ ID NO: 6) | EAITTVGAMDY (SEQ ID NO: 13) |
| 4 | DYNMD (SEQ ID NO: 1) | QINPNNGLIFFNQKFQG (SEQ ID NO: 7) | EAITTVGAMDY (SEQ ID NO: 13) |
| 5 | DYNMD (SEQ ID NO: 1) | QINPNNGLIFFNQKFKG (SEQ ID NO: 8) | EAITTVGAMDY (SEQ ID NO: 13) |
| 6 | DYNMD (SEQ ID NO: 1) | QINPYNHLIFFNQKFKG (SEQ ID NO: 9) | EAITTVGAMDY (SEQ ID NO: 13) |
| 7 | TYGMGVS (SEQ ID NO: 2) | HIYWDDDKRYNPSLKS (SEQ ID NO: 10) | RGYDDYWGY (SEQ ID NO: 14) |
| 8 | TYGMGVS (SEQ ID NO: 2) | HIYWDDDKRYNPSLKT (SEQ ID NO: 11) | RGYDDYWGY (SEQ ID NO: 14) |
| 9 | TYGMGVG (SEQ ID NO: 3) | DIW-WDDDKYYNPSLKS (SEQ ID NO: 12) | RGHYSAMDY (SEQ ID NO: 15) |

Exemplary anti-GDF15 antibodies useful in the methods and compositions of the invention may, for example, include a light chain variable region comprising any one of the four sets of $CDR_{L1}$, $CDR_{L2}$, and $CDR_{L3}$ region sequences set forth in Table 2 below.

TABLE 2

| | $CDRL_1$ | $CDRL_2$ | $CDRL_3$ |
|---|---|---|---|
| 1 | RTSENLHNYLA (SEQ ID NO: 16) | DAKTLAD (SEQ ID NO: 18) | QHFWSSPYT (SEQ ID NO: 21) |
| 2 | RTSENLHNYLA (SEQ ID NO: 16) | DAKTLAD (SEQ ID NO: 18) | QHFWSDPYT (SEQ ID NO: 22) |
| 3 | KASQNVGTNVA (SEQ ID NO: 17) | SASYRYS (SEQ ID NO: 19) | QQYNNYPLT (SEQ ID NO: 23) |
| 4 | KASQNVGTNVA (SEQ ID NO: 17) | SPSYRYS (SEQ ID NO: 20) | QQYNSYPHT (SEQ ID NO: 24) |

Exemplary anti-GDF15 antibodies useful in the practice of the invention are described in U.S. Patent Publication No. US 2014-0193427-A1, including 01G06, 03G05, 04F08, 06C11, 08G01, 14F11, 17B11, as well as human or humanized forms thereof. In certain embodiments, the antibodies disclosed herein (e.g., 01G06, 03G05, 04F08, 06C11, 08G01, 14F11, or 17B11, or humanized forms thereof) are used to treat CKD or another kidney-related disease or disorder who exhibits symptoms of CKD or who is diagnosed as having CKD or at risk of having CKD. In some embodiments, the antibodies reverse a symptom or characteristic of CKD or another kidney-related disease or disorder by at least 2%, 5%, 10%, 15%, 20%, 25%, 30% or 35%.

In a preferred embodiment, an anti-GDF15 antibody useful in the practice of the invention is referred to as 01G06 in U.S. Patent Publication No. US 2014-0193427-A1. Humanized forms of the 01G06 antibody are listed below together with the amino acid sequences of their respective heavy and light chain variable regions. Exemplary humanized anti-GDF15 antibodies include: Hu01G06-1; Hu01G06-46; Hu01G06-52; Hu01G06-100; Hu01G06-101; Hu01G06-102; Hu01G06-103; Hu01G06-104; Hu01G06-105; Hu01G06-106; Hu01G06-107; Hu01G06-108; Hu01G06-109; Hu01G06-110; Hu01G06-111; Hu01G06-112; Hu01G06-113; Hu01G06-114; Hu01G06-122; Hu01G06-127; Hu01G06-135; Hu01G06-138; Hu01G06-146; Hu06C11-1; Hu06C11-27; Hu06C11-30; Hu14F11-1; Hu14F11-23; Hu14F11-24; Hu14F11-39; and Hu14F11-47. The amino acid sequences for the heavy chain and light chain for each of the aforementioned antibodies is set forth below in Table 3.

TABLE 3

| Antibody Name | Light Chain | Heavy Chain |
|---|---|---|
| 01G06 (murine) | SEQ ID NO: 25 | SEQ ID NO: 37 |
| Hu01G06-1 | SEQ ID NO: 26 | SEQ ID NO: 38 |

TABLE 3-continued

| Antibody Name | Light Chain | Heavy Chain |
|---|---|---|
| Hu01G06-46 | SEQ ID NO: 27 | SEQ ID NO: 39 |
| Hu01G06-52 | SEQ ID NO: 27 | SEQ ID NO: 40 |
| Hu01G06-100 | SEQ ID NO: 27 | SEQ ID NO: 41 |
| Hu01G06-101 | SEQ ID NO: 27 | SEQ ID NO: 42 |
| Hu01G06-102 | SEQ ID NO: 27 | SEQ ID NO: 43 |
| Hu01G06-103 | SEQ ID NO: 27 | SEQ ID NO: 44 |
| Hu01G06-104 | SEQ ID NO: 27 | SEQ ID NO: 45 |
| Hu01G06-105 | SEQ ID NO: 28 | SEQ ID NO: 41 |
| Hu01G06-106 | SEQ ID NO: 28 | SEQ ID NO: 42 |
| Hu01G06-107 | SEQ ID NO: 28 | SEQ ID NO: 43 |
| Hu01G06-108 | SEQ ID NO: 28 | SEQ ID NO: 44 |
| Hu01G06-109 | SEQ ID NO: 28 | SEQ ID NO: 45 |
| Hu01G06-110 | SEQ ID NO: 29 | SEQ ID NO: 41 |
| Hu01G06-111 | SEQ ID NO: 29 | SEQ ID NO: 42 |
| Hu01G06-112 | SEQ ID NO: 29 | SEQ ID NO: 43 |
| Hu01G06-113 | SEQ ID NO: 29 | SEQ ID NO: 44 |
| Hu01G06-114 | SEQ ID NO: 29 | SEQ ID NO: 45 |
| Hu01G06-122 | SEQ ID NO: 29 | SEQ ID NO: 46 |
| Hu01G06-127 | SEQ ID NO: 30 | SEQ ID NO: 47 |
| Hu01G06-135 | SEQ ID NO: 29 | SEQ ID NO: 48 |
| Hu01G06-138 | SEQ ID NO: 29 | SEQ ID NO: 49 |
| Hu01G06-146 | SEQ ID NO: 30 | SEQ ID NO: 49 |
| 06C11 (murine) | SEQ ID NO: 31 | SEQ ID NO: 50 |
| Hu06C11-1 | SEQ ID NO: 32 | SEQ ID NO: 38 |
| Hu06C11-27 | SEQ ID NO: 33 | SEQ ID NO: 51 |
| Hu06C11-30 | SEQ ID NO: 33 | SEQ ID NO: 52 |
| 14F11 (murine) | SEQ ID NO: 34 | SEQ ID NO: 53 |
| Hu14F11-1 | SEQ ID NO: 35 | SEQ ID NO: 54 |
| Hu14F11-23 | SEQ ID NO: 35 | SEQ ID NO: 55 |
| Hu14F11-24 | SEQ ID NO: 32 | SEQ ID NO: 54 |
| Hu14F11-39 | SEQ ID NO: 36 | SEQ ID NO: 56 |
| Hu14F11-47 | SEQ ID NO: 36 | SEQ ID NO: 57 |

It is understood that the antibodies described herein can be designed, tested, and formulated using techniques known in the art.

```
                                                          SEQ ID NO: 25
  1 diqmtqspas lsasvgetvt itcrtsenlh nylawyqqkq gkspqllvyd aktladgvps 61 rfsgsgsgtq yslkinslqp edfgsyycqh fwsspytfgg gtkleikrad aaptvsifpp 121 sseqltsgga svvcflnnfy pkdinvkwki dgserqngvl nswtdqdskd stysmsstlt 181 ltkdeyerhn sytceathkt stspivksfn rnec SEQ ID NO: 26
  1 diqmtqspas lsasvgetvt itcrtsenlh nylawyqqkq gkspqllvyd aktladgvps 61 rfsgsgsgtq yslkinslqp edfgsyycqh fwsspytfgg gtkleikrtv aapsvfifpp 121 sdeqlksgta svvcllnnfy preakvqwkv dnalqsgnsq esvteqdskd styslsstlt 181 lskadyekhk vyacevthqg lsspvtksfn rgec SEQ ID NO: 27
  1 diqmtqspss lsasvgdrvt itcrtsenlh nylawyqqkp gkspkllvyd aktladgvps 61 rfsgsgsgtd ytltisslqp edfatyycqh fwsspytfgq gtkleikrtv aapsvfifpp 121 sdeqlksgta svvcllnnfy preakvqwkv dnalqsgnsq esvteqdskd styslsstlt 181 lskadyekhk vyacevthqg lsspvtksfn rgec SEQ ID NO: 29
  1 diqmtqspss lsasvgdrvt itcrtsenlh nylawyqqkp gkapklliyd aktladgvps 61 rfsgsgsgtd ytltisslqp edfatyycqh fwsspytfgq gtkleikrtv aapsvfifpp
```

```
121  sdeqlksgta svvcllnnfy preakvqwkv dnalqsgnsq esvteqdskd styslsstlt
181  lskadyekhk vyacevthqg lsspvtksfn rgec
                            SEQ ID NO: 28
  1  diqmtqspss lsasvgdrvt itcrtsenlh nylawyqqkp gkspklliyd aktladgvps
 61  rfsgsgsgtd ytltisslqp edfatyycqh fwsspytfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
                                                         SEQ ID NO: 32
  1  divmtqsqkf mstsvgdrvs vtckasqnvg tnvawfqqkp gqspkaliys asyrysgvpd
 61  rftgsgsgtd filtisnvqs edlaeyfcqq ynnypltfga gtklelkrtv aapsvfifpp
121  sdeqlksgta svvcllnnfy preakvqwkv dnalqsgnsq esvteqdskd styslsstlt
181  lskadyekhk vyacevthqg lsspvtksfn rgec
                                                         SEQ ID NO: 33
  1  diqmtqspss lsasvgdrvt itckasqnvg tnvawfqqkp gkapksilys asyrysgvps
 61  rfsgsgsgtd ftltisslqp edfatyycqq ynnypltfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
                            SEQ ID NO: 35
  1  divmtqsqkf mstsvgdrvs vtckasqnvg tnvawyqqkp gqspkallys psyrysgvpd
 61  rftgsgsgtd ftltisnvqs edlaeyfcqq ynsyphtfgg gtklemkrtv aapsvfifpp
121  sdeqlksgta svvcllnnfy preakvqwkv dnalqsgnsq esvteqdskd styslsstlt
181  lskadyekhk vyacevthqg lsspvtksfn rgec
                            SEQ ID NO: 36
  1  diqmtqspss lsasvgdrvt itckasqnvg tnvawfqqkp gkspkallys psyrysgvps
 61  rfsgsgsgtd ftltisslqp edfatyfcqq ynsyphtfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
                            SEQ ID NO: 37
  1  evllqqsgpe lvkpgasvki pckasgytft dynmdwvkqs hgkslewigq inpnnggiff
 61  nqkfkgkatl tvdkssntaf mevrsltsed tavyycarea ittvgamdyw gqgtsvtvss
121  akttppsvyp lapgsaaqtn smvtlgclvk gyfpepvtvt wnsgslssgv htfpavlqsd
181  lytlsssvtv psstwpsetv tcnvahpass tkvdkkivpr dcgckpcict vpevssvfif
241  ppkpkdvlti tltpkvtcvv vdiskddpev qfswfvddve vhtaqtqpre eqfnstfrsv
301  selpimhqdw lngkefkcrv nsaafpapie ktisktkgrp kapqvytipp pkeqmakdkv
361  sltcmitdff peditvewqw ngqpaenykn tqpimdtdgs yfvysklnvq ksnweagntf
421  tcsvlheglh nhhtekslsh spgk
                            SEQ ID NO: 30
  1  diqmtqspss lsasvgdrvt itcrtsenlh nylawyqqkp gkspklliyd aktladgvps
 61  rfsgsgsgtd ytltisslqp edfatyycqh fwsdpytfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
                            SEQ ID NO: 38
  1  evllqqsgpe lvkpgasvki pckasgytft dynmdwvkqs hgkslewigq inpnnggiff
 61  nqkfkgkatl tvdkssntaf mevrsltsed tavyycarea ittvgamdyw gqgtsvtvss
```

-continued

```
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
                                                         SEQ ID NO: 39
  1 qvqlvqsgae vkkpgasvkv sckasgytft dynmdwvrqa pgkslewigq inpnnggiff
 61 nqkfkgratl tvdtstntay melrslrsdd tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
                         SEQ ID NO: 40
  1 qvqlvqsgae vkkpgssvkv sckasgytft dynmdwvrqa pgkslewigq inpnnggiff
 61 nqkfkgratl tvdkstntay melsslrsed tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
                                                         SEQ ID NO: 41
  1 qvqlvqsgae vkkpgasvkv sckasgytft dynmdwvrqa pgqglewmgq inpnnggiff
 61 nqkfkgrvtl ttdtststay melrslrsdd tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
                         SEQ ID NO: 43
  1 qvqlvqsgae vkkpgasvkv sckasgytft dynmdwvrqa pgqslewmgq inpnnggiff
 61 nqkfqgrvtl ttdtststay melrslrsdd tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

```
                            SEQ ID NO: 42
  1 qvqlvqsgae vkkpgasvkv sckasgytft dynmdwvrqa pgqglewmgq inpnnggiff
 61 nqkfqgrvtl ttdtststay melrslrsdd tavyycarea ittvgamdyw gqgtivtvss
121 astkgpsvfp lapssksstg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
                            SEQ ID NO: 44
  1 qvqlvqsgae vkkpgssvkv sckasgytfs dynmdwvrqa pgqglewmgq inpnnggiff
 61 nqkfkgrvtl tadkststay melsslrsed tavyycarea ittvgamdyw gqgtivtvss
121 astkgpsvfp lapssksstg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
                            SEQ ID NO: 45
  1 qvqlvqsgae vkkpgssvkv sckasgytfs dynmdwvrqa pgqglewmgq inpnnggiff
 61 nqkfqgrvtl tadkststay melsslrsed tavyycarea ittvgamdyw gqgtivtvss
121 astkgpsvfp lapssksstg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
                            SEQ ID NO: 46
  1 qvqlvqsgae vkkpgasvkv sckasgytft dynmdwvrqa pgqslewmgq inpynhliff
 61 nqkfqgrvtl ttdtststay melrslrsdd tavyycarea ittvgamdyw gqgtivtvss
121 astkgpsvfp lapssksstg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
                            SEQ ID NO: 47
  1 qvqlvqsgae vkkpgasvkv sckasgytft dynmdwvrqa pgqslewmgq inpnngliff
 61 nqkfqgrvtl ttdtststay melrslrsdd tavyycarea ittvgamdyw gqgtivtvss
121 astkgpsvfp lapssksstg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
```

-continued

```
361 mtknqvsltc lvkgfypsdi avewesngqp ennykttppv ldsdgsffly skltvdksrw
421 qqgnvfscsv mhealhnhyt qkslslspgk
```

SEQ ID NO: 48
```
  1 qvqlvqsgae vkkpgssvkv sckasgytfs dynmdwvrqa pgqglewmgq inpnngliff
 61 nqkfkgrvtl tadkststay melsslrsed tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

SEQ ID NO: 49
```
  1 qvqlvqsgae vkkpgssvkv sckasgytfs dynmdwvrqa pgqglewmgq inpynhliff
 61 nqkfkgrvtl tadkststay melsslrsed tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

SEQ ID NO: 38
```
  1 evllqqsgpe lvkpgasvki pckasgytft dynmdwvkqs hgkslewigq inpnnggiff
 61 nqkfkgkatl tvdkssntaf mevrsltsed tavyycarea ittvgamdyw gqgtsvtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

SEQ ID NO: 51
```
  1 qvtlkesgpa lvkptqtltl tctfsgfsln tygmgvswir qppgkalewl ahiywdddkr
 61 ynpslktrlt iskdtsknqv vltitnvdpv dtavyycaqr gyddywgywg qgtivtissa
121 stkgpsvfpl apssksrsgg taalgclvkd yfpepvtvsw nsgaltsgvh tfpavlqssg
181 lyslssvvtv pssslgtqty icnvnhkpsn tkvdkrvepk scdkthtcpp cpapellggp
241 svflfppkpk dtlmisrtpe vtcvvvdvsh edpevkfnwy vdgvevhnak tkpreeqyns
301 tyrvvsvltv lhqdwlngke ykckvsnkal papiektisk akgqprepqv ytlppsreem
361 tknqvsltcl vkgfypsdia vewesngqpe nnykttppvl dsdgsfflys kltvdksrwq
421 qgnvfscsvm healhnhytq kslslspgk
```

SEQ ID NO: 52
```
  1 qvtlkesgpt lvkptqtltl tctfsgfsln tygmgvswir qppgkglewl ahiywdddkr
 61 ynpslksrlt itkdtsknqv vltitnmdpv dtatyycaqr gyddywgywg qgtivtvssa
121 stkgpsvfpl apssksrsgg taalgclvkd yfpepvtvsw nsgaltsgvh tfpavlqssg
181 lyslssvvtv pssslgtqty icnvnhkpsn tkvdkrvepk scdkthtcpp cpapellggp
```

-continued

```
241 svflfppkpk dtlmisrtpe vtcvvvdvsh edpevkfnwy vdgvevhnak tkpreeqyns 301 tyrvvsvltv lhqdwlngke ykckvsnkal papiektisk akgqprepqv ytlppsreem 361 tknqvsltcl vkgfypsdia vewesngqpe nnykttppvl dsdgsfflys kltvdksrwq 421 qgnvfscsvm healhnhytq kslslspgk
```

SEQ ID NO: 54
```
  1 qvtlkesgpg ilqpsqtlsl tcsfsgfsls tygmgvgwir qpsgkglewl adiwwdddky 61 ynpslksrlt iskdtssnev flkiaivdta dtatyycarr ghysamdywg qgtsvtvssa 121 stkgpsvfpl apsskstsgg taalgclvkd yfpepvtvsw nsgaltsgvh tfpavlqssg 181 lyslssvvtv pssslgtqty icnvnhkpsn tkvdkrvepk scdkthtcpp cpapellggp 241 svflfppkpk dtlmisrtpe vtcvvvdvsh edpevkfnwy vdgvevhnak tkpreeqyns 301 tyrvvsvltv lhqdwlngke ykckvsnkal papiektisk akgqprepqv ytlppsreem 361 tknqvsltcl vkgfypsdia vewesngqpe nnykttppvl dsdgsfflys kltvdksrwq 421 qgnvfscsvm healhnhytq kslslspgk
```

SEQ ID NO: 55
```
  1 qvtlkesgpg ilqpsqtlsl tcsfsgfsln tygmgvswir qpsgkglewl ahiywdddkr 61 ynpslksrlt iskdasnnry flkitsvdta dtatyycaqr gyddywgywg qgtivtisaa 121 stkgpsvfpl apsskstsgg taalgclvkd yfpepvtvsw nsgaltsgvh tfpavlqssg 181 lyslssvvtv pssslgtqty icnvnhkpsn tkvdkrvepk scdkthtcpp cpapellggp 241 svflfppkpk dtlmisrtpe vtcvvvdvsh edpevkfnwy vdgvevhnak tkpreeqyns 301 tyrvvsvltv lhqdwlngke ykckvsnkal papiektisk akgqprepqv ytlppsreem 361 tknqvsltcl vkgfypsdia vewesngqpe nnykttppvl dsdgsfflys kltvdksrwq 421 qgnvfscsvm healhnhytq kslslspgk
```

SEQ ID NO: 56
```
  1 qitlkesgpt lvkptqtltl tctfsgfsls tygmgvgwir qppgkalewl adiwwdddky 61 ynpslksrlt itkdtsknqv vltmtnmdpv dtatyycarr ghysamdywg qgtivtvssa 121 stkgpsvfpl apsskstsgg taalgclvkd yfpepvtvsw nsgaltsgvh tfpavlqssg 181 lyslssvvtv pssslgtqty icnvnhkpsn tkvdkrvepk scdkthtcpp cpapellggp 241 svflfppkpk dtlmisrtpe vtcvvvdvsh edpevkfnwy vdgvevhnak tkpreeqyns 301 tyrvvsvltv lhqdwlngke ykckvsnkal papiektisk akgqprepqv ytlppsreem 361 tknqvsltcl vkgfypsdia vewesngqpe nnykttppvl dsdgsfflys kltvdksrwq 421    nvfscsvm healhnhytq kslslspgk
```

SEQ ID NO: 57
```
  1 qvtlkesgpa lvkptqtltl tctfsgfsls tygmgvgwir qppgkalewl adiwwdddky 61 ynpslksrlt iskdtsknqv vltmtnmdpv dtavyycarr ghysamdywg qgtivtvssa 121 stkgpsvfpl apsskstsgg taalgclvkd yfpepvtvsw nsgaltsgvh tfpavlqssg 181 lyslssvvtv pssslgtqty icnvnhkpsn tkvdkrvepk scdkthtcpp cpapellggp 241 svflfppkpk dtlmisrtpe vtcvvvdvsh edpevkfnwy vdgvevhnak tkpreeqyns 301 tyrvvsvltv lhqdwlngke ykckvsnkal papiektisk akgqprepqv ytlppsreem 361 tknqvsltcl vkgfypsdia vewesngqpe nnykttppvl dsdgsfflys kltvdksrwq 421 qgnvfscsvm healhnhytq kslslspgk
```

SEQ ID NO: 50
```
  1 qvtlkesgpg ilqpsqtlsl tcsfsgfsln tygmgvswir qpsgkglewl ahiywdddkr 61 ynpslksrlt iskdasnnry flkitsvdta dtatyycaqr gyddywgywg qgtivtisaa
```

-continued

```
121  kttppsvypl  apgsaaqtns  mvtlgclvkg  yfpepvtvtw  nsgslssgvh  tfpavlqsdl 181  ytlsssvtvp  sstwpsetvt  cnvahpasst  kvdkkivprd  cgckpcictv  pevssvfifp 241  pkpkdvltit  ltpkvtcvvv  diskddpevq  fswfvddvev  htaqtqpree  qfnstfrsys 301  elpimhqdwl  ngkefkcrvn  saafpapiek  tisktkgrpk  apqvytippp  keqmakdkvs 361  ltcmitdffp  editvewqwn  gqpaenyknt  qpimdtdgsy  fvysklnvqk  snweagntft 421  csvlheglhn  hhtekslshs  pgk
```

SEQ ID NO: 31
```
  1  divmtqsqkf  mstsvgdrvs  vtckasqnvg  tnvawfqqkp  gqspkaliys  asyrysgvpd 61  rftgsgsgtd  filtisnvqs  edlaeyfcqq  ynnypltfga  gtklelkrad  aaptvsifpp 121  sseqltsgga  svvcflnnfy  pkdinvkwki  dgserqngvl  nswtdqdskd  stysmsstlt 181  ltkdeyerhn  sytceathkt  stspivksfn  rnec
```

SEQ ID NO: 53
```
  1  qvtlkesgpg  ilqpsqtlsl  tcsfsgfsls  tygmgvgwir  qpsgkglewl  adiwwdddky 61  ynpslksrlt  iskdtssnev  flkiaivdta  dtatyycarr  ghysamdywg  qgtsvtvssa 121  kttppsvypl  apgsaaqtns  mvtlgclvkg  yfpepvtvtw  nsgslssgvh  tfpavlqsdl 181  ytlsssvtvp  sstwpsetvt  cnvahpasst  kvdkkivprd  cgckpcictv  pevssvfifp 241  pkpkdvltit  ltpkvtcvvv  diskddpevq  fswfvddvev  htaqtqpree  qfnstfrsys 301  elpimhqdwl  ngkefkcrvn  saafpapiek  tisktkgrpk  apqvytippp  keqmakdkvs 361  ltcmitdffp  editvewqwn  gqpaenyknt  qpimdtdgsy  fvysklnvqk  snweagntft 421  csvlheglhn  hhtekslshs  pgk
```

SEQ ID NO: 34
```
  1  divmtqsqkf  mstsvgdrvs  vtckasqnvg  tnvawyqqkp  gqspkaliys  psyrysgvpd 61  rftgsgsgtd  ftltisnvqs  edlaeyfcqq  ynsyphtfgg  gtklemkrad  aaptvsifpp 121  sseqltsgga  svvcflnnfy  pkdinvkwki  dgserqngvl  nswtdqdskd  stysmsstlt 181  ltkdeyerhn  sytceathkt  stspivksfn  rnec
```

The antibody may be a neutralizing antibody, which reduces GDF15 activity. For example, the antibody may reduce GDF15 activity in an in vivo assay (see, e.g., Johnen et al., 2007, NATURE MEDICINE 13:1333-1340) by at least 10%, preferably 20%, 30% or 40%, and more preferably at least about 50%, 60%, 80% or 90% of GDF15 compared to GDF15 activity measured in the same assay under the same conditions in the absence of the antibody. The antibody may selectively and/or significantly reduce or inhibit the binding of GDF15 to its endogenous receptor. As used herein, the term "significantly reduces or inhibits binding" of GDF15 to its receptor is understood to mean that the antibody inhibits GDF15 binding with a potency or percent inhibition that measures at least 10%, preferably 20%, 30% or 40%, and more preferably at least about 50%, 60%, 80% or 90% of GDF15 [serum level/activity] in the absence of said antibody. Binding can be measured using a direct or sandwich enzyme-linked immunosorbent assay (ELISA), as described, e.g., in Tsai et al., 2013, PLOS ONE, 8: e55174. As used herein, the term "selectively" in the context of an antibody that binds to GDF15 or GDF15 receptor is understood to mean that the antibody binds GDF15 or a GDF15 receptor with a binding affinity that is at least two, three, four, five or ten times greater than that of a functionally unrelated protein or another member of the TGF-β superfamily or a receptor of a member of the TGF-β superfamily.

Methods for reducing or eliminating the antigenicity of antibodies and antibody fragments are known in the art. When the antibodies are to be administered to a human, the antibodies preferably are "humanized" to reduce or eliminate antigenicity in humans. Preferably, each humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, PROC. NAT. ACAD. SCI. 81:6851-6855, Neuberger et al., 1984, NATURE 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-GDF15 antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter);

U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al., 1986, NATURE 321: 522-525; Riechmann et al., 1988, NATURE 332: 323-327; Verhoeyen et al., 1988, SCIENCE 239: 1534-1536; and Winter, 1998, FEBS LETT 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. IMMUNOL. 169:1119-1125.

Other methods to reduce immunogenicity include "reshaping," "hyperchimerization," and "veneering/resurfacing." See, e.g., Vaswami et al., 1998, ANNALS OF ALLERGY, ASTHMA, & IMMUNOL. 81:105; Roguska et al., 1996, PROT. ENGINEER 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, NY), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, CA). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., NATURE 368:856-859, 1994; Fishwild et al., NATURE BIOTECHNOLOGY 14:845-851, 1996; and Mendez et al., NATURE GENETICS 15:146-156, 1997. Fully human mAbs can also be prepared and optimized from phage display libraries by techniques referenced in, e.g., Knappik et al., J. MOL. BIOL. 296:57-86, 2000; and Krebs et al., J. IMMUNOL. METH. 254: 67-84 2001).

It is contemplated that variants and derivatives of GDF15 that act as decoys can be useful in the practice of the invention. For example, through deletion analysis, it may be possible to identify smaller biologically active fragments of GDF15 that compete with endogenous GDF15 for its cognate receptor. Similarly, it is possible to create soluble biologically active fragments of the GDF15 receptor that compete with endogenous GDF15 receptor for available GDF. For example, "biologically active fragments" include, but are not limited to, fragments of a naturally-occurring GDF15 (or homolog) or a GDF15 receptor (or homolog) that compete with endogenous GDF15 or an endogenous GDF15 receptor, respectively, for binding to a cognate binding partner (e.g., GDF15 receptor or GDF15, respectively).

It is contemplated that antisense nucleic acids (DNA and RNA) and small interfering nucleic acids (e.g., siRNAs) can be designed and used using techniques known in the art. Exemplary siRNA inhibitors of GDF15 include siRNAs from Santa Cruz Biotech (Catalog No. sc-39799, targeting mouse GDF15; and Catalog No. sc-39798, targeting human GDF15), siRNAs from Life Technologies (Cat. Nos. AM16708, 4392420, and 1299001, targeting human GDF15; and Cat. Nos. 1320001 and 4390771, targeting mouse GDF15; and Cat. Nos. 1330001 and 4390771, targeting rat GDF15), siRNAs from Fisher Scientific (Catalog No. NC0683807, targeting human GDF15), siRNAs from Origene (Catalog No. SR306321, targeting human GDF15), siRNAs from amsbio (Catalog No. SR509800, targeting rate GDF15), siRNAs from Dharmacon (including Catalog No. D-019875-02, targeting human GDF15), siRNAs from Sigma-Aldrich (Catalog No. EHU052901, targeting human GDF15), and siRNAs described in Kim et al., 2005, MOLECULAR CANCER THERAPEUTICS, 4:487-493, Chang et al., 2007, MOL. CANCER THERAPEUTICS, 6:2271-2279, and Boyle et al., 2009, J. INVEST. DERMATOL., 129:383-391.

IV. Formulation and Delivery of GDF15 Modulators

Pharmaceutical compositions containing GDF15 modulators, such as those disclosed herein, can be formulated into dosage forms or dosage units using standard formulation techniques. However, the pharmaceutical composition should be formulated to be compatible with its intended route of administration.

The compositions described herein can be administered to a subject via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intraocular, intrathecal, transdermal, transpleural, intraarterial, topical, inhalational (e.g., as mists of sprays), mucosal (such as via nasal mucosa), subcutaneous, transdermal, gastrointestinal, intraarticular, intracistemal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection). A preferred route of administration for GDF15 modulators, such as an antibody, is via intravenous infusion.

Useful formulations can be prepared by methods well known in the pharmaceutical art. For example, see REMINGTON'S PHARMACEUTICAL SCIENCES, 18th ed. (Mack Publishing Company, 1990). Formulation components suitable for parenteral administration include a sterile diluent such as bacteriostatic water for injection, physiological saline, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose. The carrier should be stable under the conditions of manufacture and storage, and should be preserved against microorganisms. In some embodiments, a GDF15 modulator (e.g., an antibody) is lyophilized, and then reconstituted in buffered saline, at the time of administration.

For therapeutic use, a GDF15 modulator (e.g., an antibody) preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

The pharmaceutical compositions preferably are sterile. Sterilization can be accomplished, for example, by filtration through sterile filtration membranes. Where the composition is lyophilized, filter sterilization can be conducted prior to or following lyophilization and reconstitution.

Generally, a therapeutically effective amount of active component is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of a GDF15 modulator (e.g., an antibody), the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the GDF15 modulator (e.g., an antibody), and the disease being treated. Exemplary dosing frequencies are once per day, once per week and once every two weeks.

The optimal effective amount of the compositions can be determined empirically and will depend on the type and severity of the disease, route of administration, disease progression and health, mass and body area of the subject. Such determinations are within the skill of one in the art. Examples of dosages of GDF15 modulator molecules which can be used for methods described herein include, but are not limited to, an effective amount within the dosage range of any of about 0.01 µg/kg to about 300 mg/kg, or within about 0.1 µg/kg to about 40 mg/kg, or with about 1 µg/kg to about 20 mg/kg, or within about 1 µg/kg to about 10 mg/kg. For example, when administered subcutaneously, the composition may be administered at low microgram ranges, including for example about 0.1 µg/kg or less, about 0.05 µg/kg or less, or 0.01 µg/kg or less.

In certain embodiments, the amount of GDF15 modulators administered to a subject is about 10 µg to about 500 mg per dose, including for example any of about 10 µg to about 50 µg, about 50 µg to about 100 µg, about 100 µg to about 200 µg, about 200 µg to about 300 µg, about 300 µg to about 500 µg, about 500 µg to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, or about 400 mg to about 500 mg per dose. In certain embodiments, a GDF15 modulator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the GDF15 modulator can be administered. In one embodiment, 0.5 mg of GDF15 modulator is administered locally. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of GDF15 modulator is administered locally.

The GDF15 modulator compositions may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgical implanted in various locations in the body.

In certain embodiments of the invention, the dosing of the GDF15 modulator is titrated such that the dose is sufficient to reduce or prevent adverse effects, but yet fully or partially inhibit the activity of the GDF15.

In some aspects, the activity of GDF15 can be modulated in a target cell using antisense nucleic acids or small interfering nucleic acids. Modulation can be achieved using expression constructs known in the art, e.g., naked DNA constructs, DNA vector based constructs, and/or viral vector and/or viral based constructs to express nucleic acids encoding an anti-GDF15 siRNA or antisense molecule.

Exemplary DNA constructs and the therapeutic use of such constructs are well known to those of skill in the art (see, e.g., Chiarella et al., 2008, RECENT PATENTS ANTI-INFECT. DRUG DISC., 3:93-101; Gray et al., 2008, EXPERT OPIN. BIOL. THER., 8:911-922; Melman et al., 2008, HUM. GENE THER., 17:1165-1176). Naked DNA constructs typically include one or more therapeutic nucleic acids (e.g., GDF15 modulators) and a promoter sequence. A naked DNA construct can be a DNA vector, commonly referred to as pDNA. Naked DNA typically do not integrate into chromosomal DNA. Generally, naked DNA constructs do not require, or are not used in conjunction with, the presence of lipids, polymers, or viral proteins. Such constructs may also include one or more of the non-therapeutic components described herein.

DNA vectors are known in the art and typically are circular double stranded DNA molecules. DNA vectors usually range in size from three to five kilo-base pairs (e.g., including inserted therapeutic nucleic acids). Like naked DNA, DNA vectors can be used to deliver and express one or more therapeutic proteins in target cells. DNA vectors do not integrate into chromosomal DNA.

Generally, DNA vectors include at least one promoter sequence that allows for replication in a target cell. Uptake of a DNA vector may be facilitated by combining the DNA vector with, for example, a cationic lipid, and forming a DNA complex. Typically, viral vectors are double stranded circular DNA molecules that are derived from a virus. Viral vectors typically are larger in size than naked DNA and DNA vector constructs and have a greater capacity for the introduction of foreign (i.e., not virally encoded) genes. Like naked DNA and DNA vectors, viral vectors can be used to deliver and express one or more therapeutic nucleic acids in target cells. Unlike naked DNA and DNA vectors, certain viral vectors stably incorporate themselves into chromosomal DNA. Typically, viral vectors include at least one promoter sequence that allows for replication of one or more vector encoded nucleic acids, e.g., a therapeutic nucleic acid, in a host cell. Viral vectors may optionally include one or more non-therapeutic components described herein. Advantageously, uptake of a viral vector into a target cell does not require additional components, e.g., cationic lipids. Rather, viral vectors transfect or infect cells directly upon contact with a target cell.

The approaches described herein include the use of retroviral vectors, adenovirus-derived vectors, and/or adeno-associated viral vectors as recombinant gene delivery systems for the transfer of exogenous genes in vivo, particularly into humans. Protocols for producing recombinant retroviruses and for infecting cells in vitro or in vivo with such viruses can be found in CURRENT PROTOCOLS IN MOLECULAR BIOLOGY, Ausubel, F. M. et al. (eds.) Greene Publishing Associates, 1989, Sections 9.10-9.14, and other standard laboratory manuals.

Viruses that are used as transduction agents of DNA vectors and viral vectors such as adenoviruses, retroviruses, and lentiviruses may be used in practicing the present invention. Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus. As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV).

In certain embodiments, an adenovirus can be used in accordance with the methods described herein. The genome of an adenovirus can be manipulated such that it encodes and expresses a gene product of interest but is inactivated in terms of its ability to replicate in a normal lytic viral life cycle. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors.

Adeno-associated virus is a naturally occurring defective virus that requires another virus, such as an adenovirus or a herpes virus, as a helper virus for efficient replication and a productive life cycle. It is also one of the few viruses that may integrate its DNA into nondividing cells, and exhibits a high frequency of stable integration.

In various embodiments, one or more viral vectors that expresses a therapeutic transgene or transgenes encoding a GDF15 modulator is administered by direct injection to a cell, tissue, or organ of a subject, in vivo. In various other embodiments, cells are transduced in vitro or ex vivo with such a vector encapsulated in a virus, and optionally expanded ex vivo. The transduced cells are then administered to the subject. Cells suitable for transduction include, but are not limited to stem cells, progenitor cells, and differentiated cells. In certain embodiments, the transduced cells are embryonic stem cells, bone marrow stem cells, umbilical cord stem cells, placental stem cells, mesenchymal stem cells, neural stem cells, liver stem cells, pancreatic stem cells, cardiac stem cells, kidney stem cells, or hematopoietic stem cells.

In particular embodiments, host cells transduced with viral vector of the invention that expresses one or more polypeptides, are administered to a subject to treat and/or prevent an auditory disease, disorder, or condition. Other methods relating to the use of viral vectors, which may be utilized according to certain embodiments of the present invention, can be found in, e.g., Kay, 1997, CHEST, 111 (6 Supp.): 138S-142S; Ferry et al., 1998, HUM. GENE THER., 9:1975-81; Shiratory et al., 1999, LIVER, 19:265-74; Oka et al., 2000, CURR. OPIN. LIPIDOL., 11:179-86; Thule et al., 2000, GENE THER., 7: 1744-52; Yang, 1992, CRIT. REV. BIOTECHNOL., 12:335-56; Alt, 1995, J. HEPATOL., 23:746-58; Brody et al., 1994, ANN. N. Y. ACAD. SCI., 716:90-101; Strayer, 1999, EXPERT OPIN. INVESTIG. DRUGS, 8:2159-2172; Smith-Arica et al., 2001, CURR. CARDIOL. REP., 3:43-49; and Lee et al., 2000, NATURE, 408:483-8.

Certain embodiments of the invention provide conditional expression of a polynucleotide of interest. For example, expression is controlled by subjecting a cell, tissue, organism, etc., to a treatment or condition that causes the polynucleotide to be expressed or that causes an increase in or decrease in expression of the polynucleotide encoded by the polynucleotide of interest. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, GENE, 323: 67), the cumate inducible gene switch (WO 2002/088346), tetracycline-dependent regulatory systems, etc.

Conditional expression can also be achieved by using a site specific DNA recombinase. According to certain embodiments of the invention the vector comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, 1993, CURRENT OPINION IN BIOTECHNOLOGY, 3:699-707), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IHF, Xis, Flp, Fis, Hin, Gin, OC31, Cin, Tn3 resolvase, TndX, XerC, XerD, TnpX, Hjc, Gin, SpCCE1. and ParA.

The vectors may comprise one or more recombination sites for any of a wide variety of site specific recombinases. It is to be understood that the target site for a site specific recombinase is in addition to any site(s) required for integration of a vector (e.g., a retroviral vector or lentiviral vector).

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al., 1977, CELL, 11:223-232) and adenine phosphoribosyltransferase (Lowy et al., 1990, CELL, 22:817-823) genes which can be employed in tk- or aprt-cells, respectively.

All the molecular biological techniques required to generate an expression construct described herein are standard techniques that will be appreciated by one of skill in the art.

In certain embodiments, DNA delivery may occur parenterally, intravenously, intramuscularly, or even intraperitoneally as described, for example, in U.S. Pat. Nos. 5,543,158; 5,641,515; and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

In certain embodiments, DNA delivery may occur by use of liposomes, nanocapsules, microparticles, microspheres, lipid particles, vesicles, optionally mixing with cell penetrating polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Exemplary formulations for ex vivo DNA delivery may also include the use of various transfection agents known in the art, such as calcium phosphate, electroporation, heat shock and various liposome formulations (i.e., lipid-mediated transfection). Particular embodiments of the invention may comprise other formulations, such as those that are well known in the pharmaceutical art, and are described, for example, in REMINGTON: THE SCIENCE AND PRACTICE OF PHARMACY, 20th Edition. Baltimore, MD: Lippincott Williams & Wilkins, 2000.

In certain embodiments, GDF15 activity is inhibited by contacting a body fluid with a composition comprising a GDF15 modulator ex vivo under conditions that permit the GDF15 modulators to reduce or inhibit GDF15 activity. Suitable body fluids include those that can be returned to the individual, such as blood, plasma, or lymph. Affinity adsorption apheresis is described generally in Nilsson et al., 1988, BLOOD, 58(1):38-44; Christie et al., 1993, TRANSFUSION, 33:234-242; Richter et al., 1997, ASAIO J., 43(1):53-59; Suzuki et al., 1994, AUTOIMMUNITY, 19: 105-112; U.S. Pat. No. 5,733,254; Richter et al., 1993, METABOL. CLIN. EXP., 42:888-894; and Wallukat et al., 1996, INT'L J. CARD., 54: 1910195.

Accordingly, the invention includes methods of treating one or more diseases described herein in a subject comprising treating the subject's blood extracoporeally (i.e., outside the body or ex vivo) with a composition comprising a GDF15 modulator under conditions that permit the modulator to reduce or inhibit GDF15 activity in the blood of the subject.

EXAMPLES

Example 1

Administration of Recombinant mFc-GDF15 Increases Blood Urea Levels

ICR SCID (spontaneous mutant T&B cell deficient) mice were injected intraperitoneally with a PBS solution (control) or 40 µg of a murine, recombinant Fc-GDF15 protein. Body weight, and molecular markers for muscle degradation (Atrogin, MurF1), adipogenesis (Glut4, Leptin, C/EPBβ) and lipid accumulation (Stearoyl-CoA desaturase, Fatty acid synthase) were measured after injection.

Figure 2A:
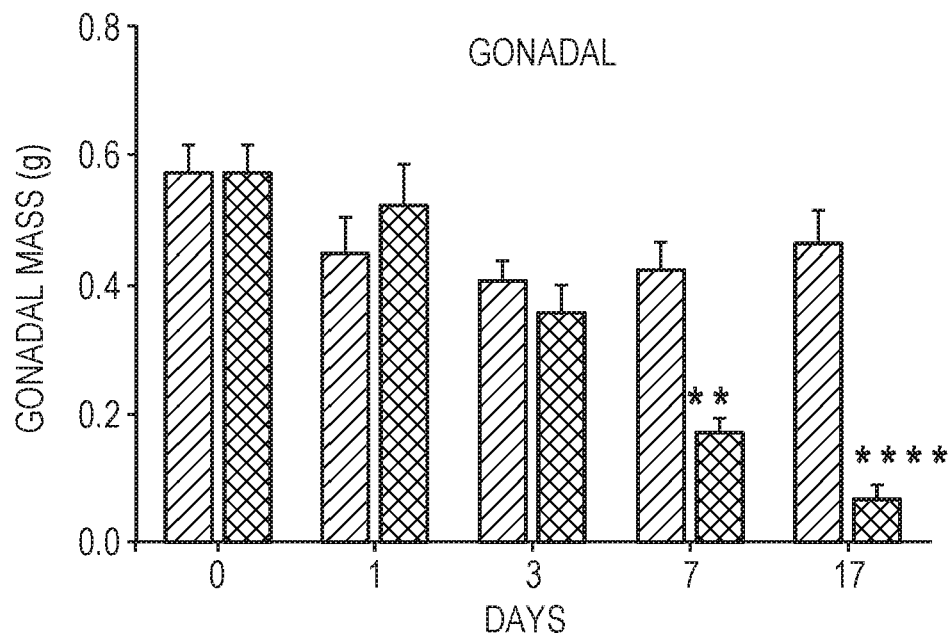
FIGS. 2A-2B are bar charts showing the effect of a single dose of 40 µg murine Fc-GDF15 recombinant protein injected intraperitoneally into mice, where both gonadal (FIG. 2A) and gastroc muscle (FIG. 2B) mass decreased significantly. For each time point, left hand bar is PBS, right-hand bar is mFc-GDF15.
Figure 2B:
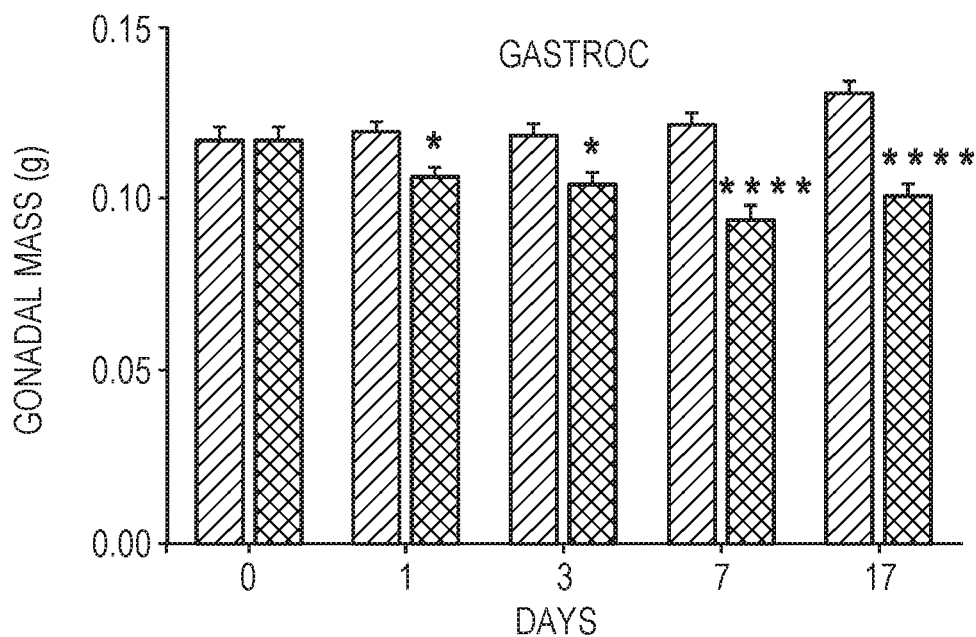

FIG. 1 shows that mice injected with Fc-GDF15 exhibited significant body weight loss. Similarly, mice injected with Fc-GDF15 exhibited significant loss of gonadal mass (FIG. 2A) and gastroc mass (FIG. 2B). The treated mice also exhibited upregulation of markers for muscle degradation (Atrogin, MurF1) and downregulation of markers of adipogenesis (Glut4, leptin) and lipid accumulation (stearoyl-CoA desaturase; fatty acid synthase).

Figure 3:
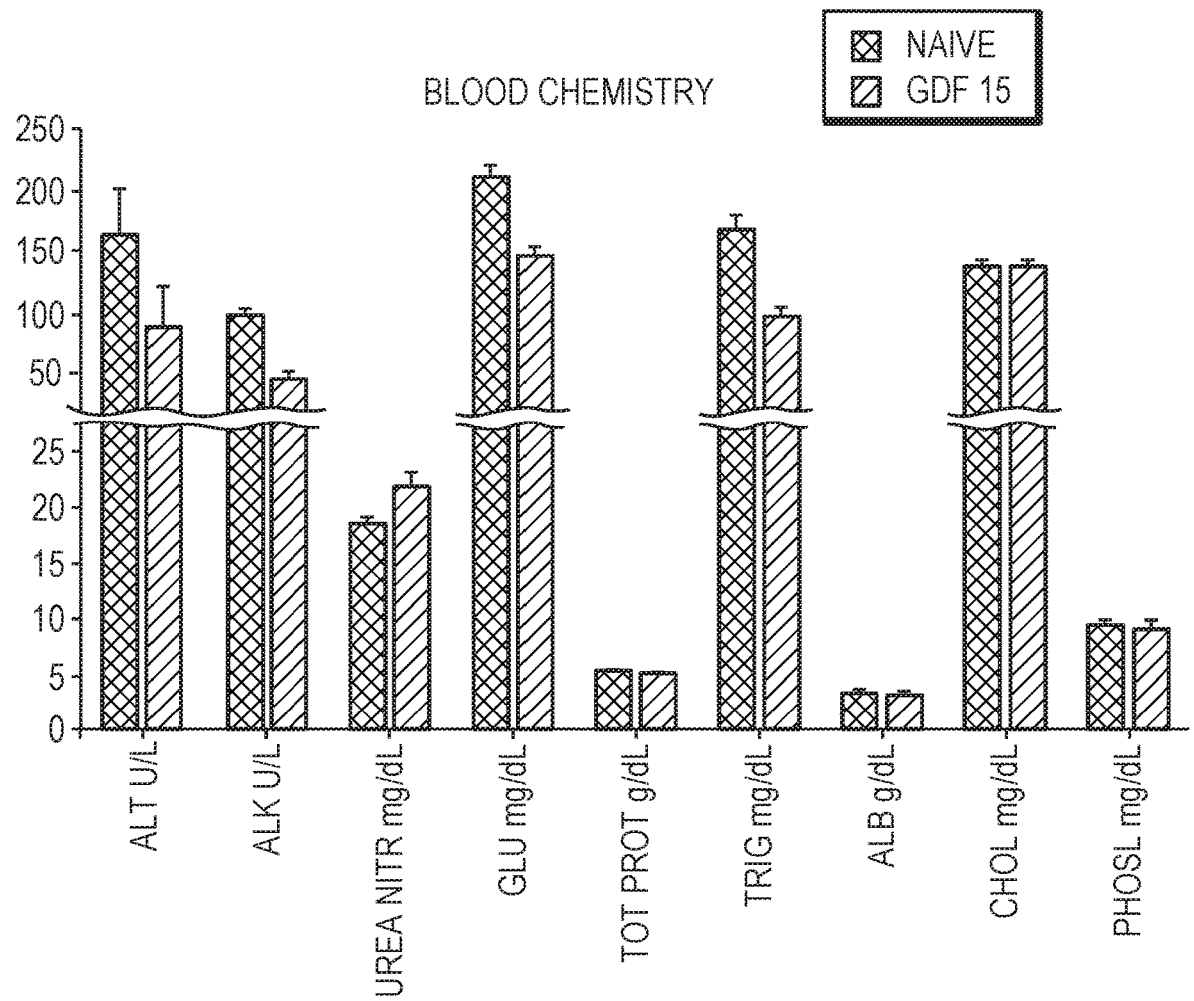
FIG. 3 is a bar chart showing the effect on mice following injection of recombinant murine Fc-GDF15. For each marker (e.g., ALT), left-hand bar is naïve, right hand bar is GDF15. Mice treated with GDF15 exhibited lower levels of liver enzymes alanine aminotransferase (ALT); alkaline phosphatase (ALK), as well as an increase in urea levels (urea nitr.) in blood, a marker of kidney impairment.

Mice treated with Fc-GDF15 also exhibited lower levels of liver enzymes (alanine aminotransferase (ALT), alkaline phosphatase (ALK); and an increase in urea levels in blood (urea nitrogen, a marker of kidney impairment) (FIG. 3), consistent with a role of GDF15 in kidney function.

Example 2

Treatment of Renal Hypotrophy in an HT-1080 Xenograft Tumor Model

This Example demonstrates the treatment of renal hypotrophy (as indicated by kidney weight loss) by an anti-GDF15 antibody (01G06) in an HT-1080 fibrosarcoma xenograft model. HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5 \times 10^6$ cells per mouse in 50% matrigel. Body weight was measured daily. When body weight reached 80%, the mice were randomized into two groups of five mice each. Each group received one of the following treatments via intraperitoneal injection: murine IgG control, murine 01G06 dosed at 2 mg/kg on day 1 and day 7. In this experiment, a group of five mice were sacrificed at the time of dosing (baseline or 80% body weight loss, without treatment) and at the end of study (seven days post dose, either mIgG or 01G06). Liver, heart, spleen, kidney, gonadal fat and the gastrocnemius muscles were removed surgically and weighed. Treatment with anti-GDF15 antibody 01G06 resulted in body weight increase to initial weight or 100% (p<0.001) (FIG. 4A), and in kidney weight increase (FIG. 4B).

Figure 4A:
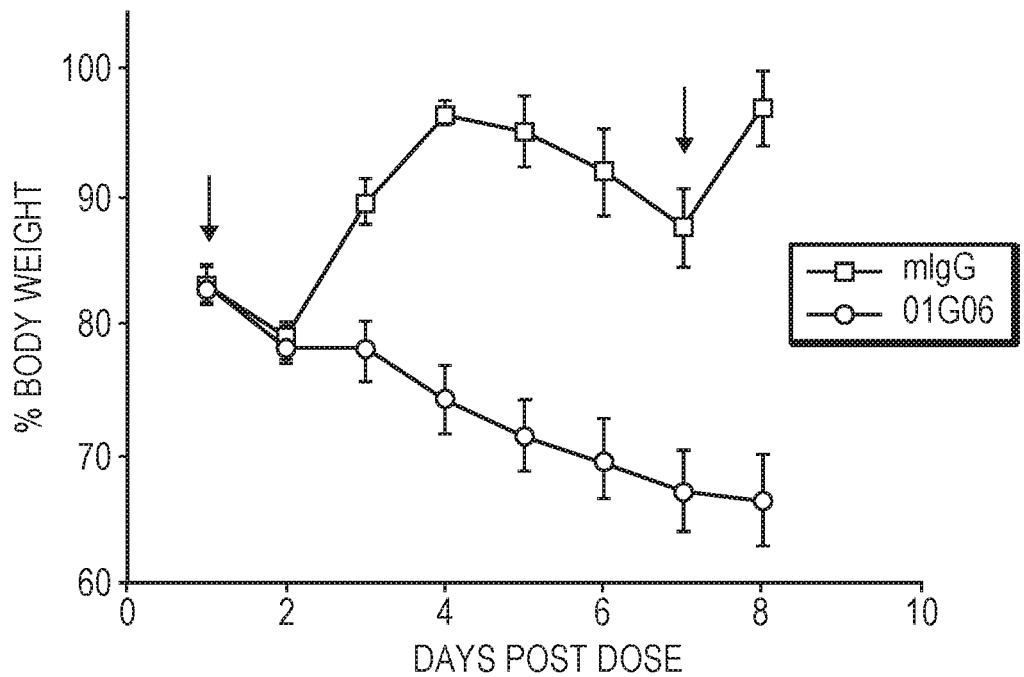
FIG. 4A is a graph showing that body weight loss is reversed in immune-incompetent mice (ICR-SCID) bearing an HT-1080 fibrosarcoma tumor xenograft model following administration of 2 mg/kg of an anti-GDF15 antibody (01G06). Arrows indicate intra-peritoneal injection of antibody.
Figure 4B:
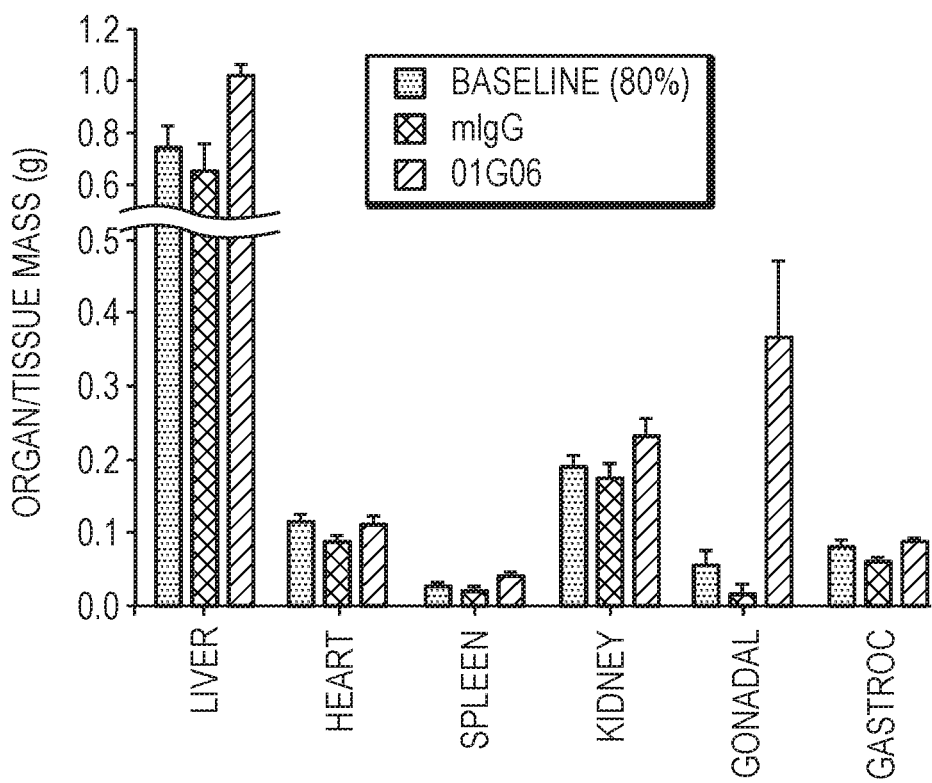
FIG. 4B is a bar chart showing that administration of the anti-GDF15 antibody increased organ mass (liver, heart, spleen, kidney) and increased tissue mass (gonadal and gastrocnemius) compared to negative control (murine IgG (●) and baseline (day 1).

As shown in FIG. 4B, a significant loss in liver, heart, spleen, kidney, gonadal fat and gastrocnemius muscle mass was observed seven days post dose with mIgG, but not in the group treated with anti-GDF15 antibody 01G06. In addition, mice treated with anti-GDF15 antibody 01G06 displayed significant liver and gonadal muscle gain compared to the baseline group (FIG. 4B).

The data in FIGS. 4A-B indicate that an anti-GDF15 antibody can reverse kidney weight loss in an HT-1080 fibrosarcoma xenograft model. Similarly, the results indicate that an anti-GDF15 antibody can reverse the loss of organ mass, such as kidney mass, loss of muscle mass, loss of fat and involuntary weight loss in an HT-1080 xenograft tumor model.

Example 3

Figure 5A:
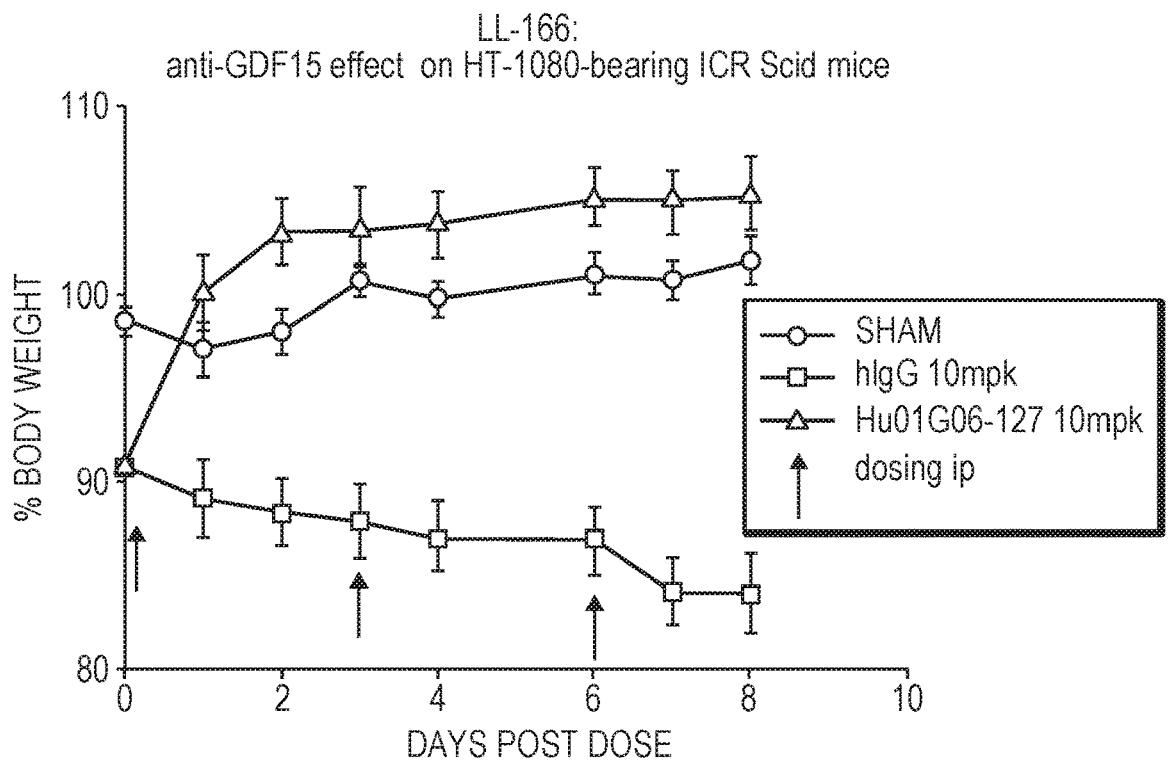
FIG. 5A is a graph showing the effect of systemic administration of anti-GDF15 antibody (Hu01G06-127) on ICR Scid mice bearing HT-1080 human tumor xenografts. Such mice exhibit significant body weight loss. Administration of anti-GDF15 antibody (▲) but not human IgG (■) reversed the loss of body weight.
Figure 5B:
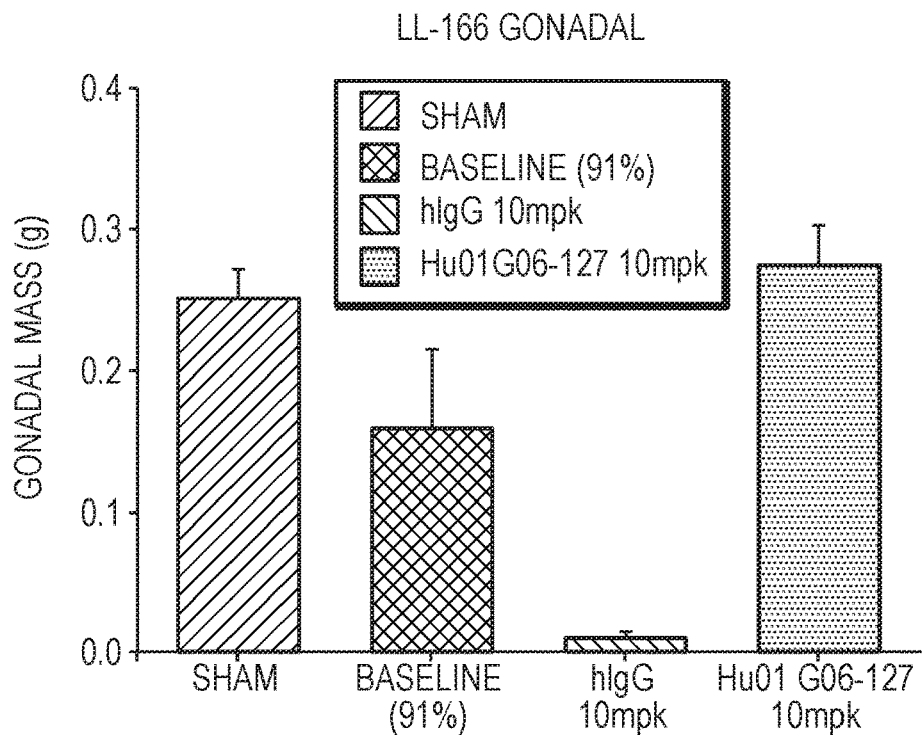
FIG. 5B is a bar chart showing that administration of an anti-GDF antibody, but not human IgG, restored gonadal mass.
Figure 6:
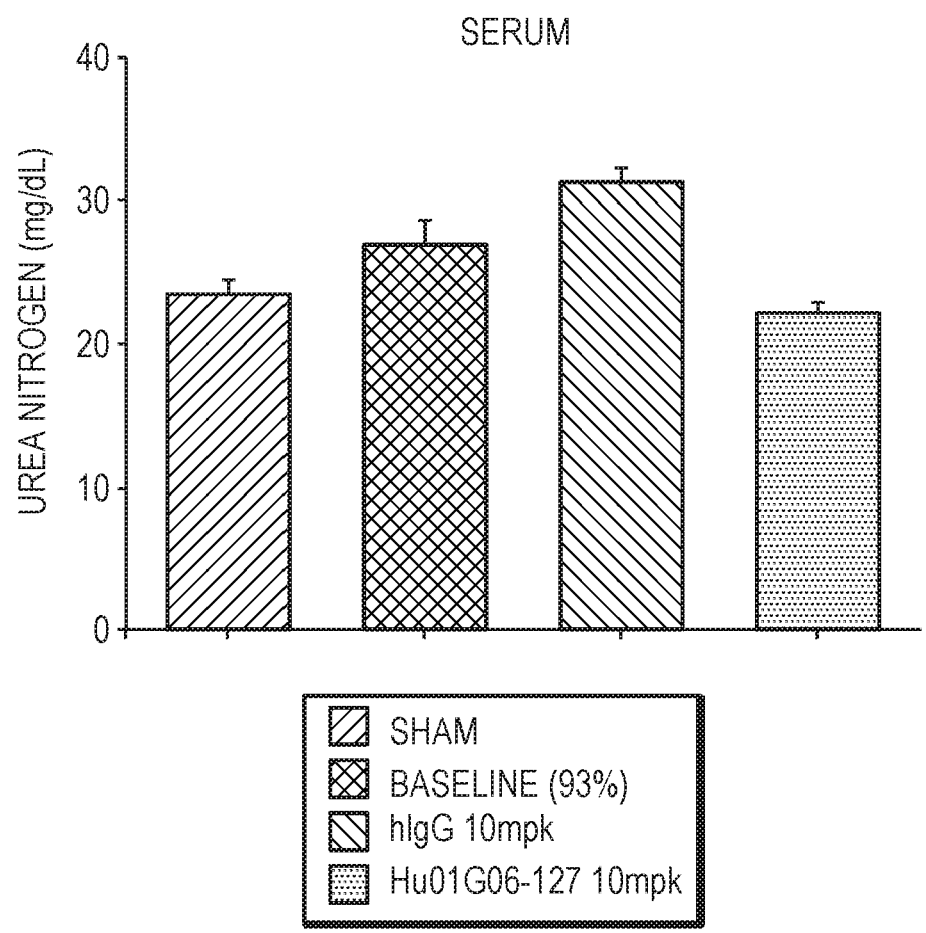
FIG. 6 is a bar chart showing the effect on serum levels of urea nitrogen following administration of antibody to GDF15. Mice bearing HT-1080 human tumor xenografts exhibited increased levels of serum urea nitrogen, a marker of kidney impairment. This increase is reversed by the administration of an anti-GDF15 antibody. Bars from left to right are SHAM, Baseline (93%), hIgG 10 mpk, and Hu01G06-127 10 mpk.

Treatment with Anti-GDF15 Antibody Reverses Elevated Levels of Urea Seen in Mice Bearing HT-1080 Human Tumor Xenographs ICR SCID (spontaneous mutant T&B cell deficient) mice bearing HT-1080 human tumor xenografts, as in Example 2, exhibit cachexia. Systemic administration of 10 mg/kg of an anti-GDF15 antibody (Hu01G06-127) but not human IgG reversed the body weight loss observed in mice bearing HT-1080 human tumor xenografts (FIG. 5A), as well gonadal weight loss (FIG. 5B). Administration of the anti-GDF15 antibody also reversed elevated levels of urea observed in mice bearing HT-1080 human tumor xenografts (FIG. 6).

Example 4

In Vivo Model of Chronic Kidney Disease

Sub-total nephrectomy, mimics the progressive renal failure after loss of renal mass in humans. As described in Ma and Fogo, 2003, KIDNEY INTERNATIONAL, 64:350-355, one kidney is removed and approximately ⅔ of the remaining kidney is ablated, resulting in reduced kidney functional relevant to progressive kidney disease. Animals are dosed with either anti-GDF15 antibody or control at the time of treatment. Animals are assessed for body and kidney size and weight, glomerular filtration rate, serum creatinine and other markers for kidney disease.

Example 5

Ureteral Obstruction Model of Progressive Renal Disease

Unilateral ureteral obstruction (UUO) in animals, as described in Chevalier et al., 2009, KIDNEY INTERNATIONAL, 75:1145-1152, is a model of renal fibrosis and chronic kidney injury. Ureteral obstruction can be accomplished by ligation, or by placement of a reversible obstruction. Animals are dosed with either anti-GDF15 antibody or control at the time of treatment. Animals are assessed for body and kidney size and weight, glomerular filtration rate, systolic blood pressure, atrophy of the tubules and tubular apoptosis. Glomerular filtrate rate can be measured following relief of UUO using standard clearance techniques.

Example 6

Treatment of Subjects Previously Treated with Other Renal Interventions

Subjects exhibiting renal hypotrophy who have previously been treated with known renal interventions, but who exhibit at least one characteristic of chronic kidney disease, are treated with an anti-GDF15 antibody. Treatment with an anti-GDF15 antibody lasts for a duration of 3 months, during which kidney size, creatinine levels, glomerular filtration rate, and renal output are monitored at regular intervals.

INCORPORATION BY REFERENCE

The entire disclosure of each of the patent documents and scientific articles referred to herein, including U.S. Patent Application Ser. No. 62/015,093, filed Jun. 20, 2014, is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. A method of decreasing blood urea nitrogen (BUN) levels in a subject with hyperuricemia, the method comprising administering an effective amount of an anti-GDF15 antibody that decreases or inhibits GDF15 activity in the subject, wherein the anti-GDF15 antibody is selected from:
   a) an antibody comprising the heavy chain sequence of SEQ ID NO:47 or 49 and the light chain sequence of SEQ ID NO:30;
   b) an antibody comprising the heavy chain sequence of SEQ ID NO:41, 42, 43, 44, 45, 46, 48, or 49 and the light chain sequence of SEQ ID NO:29;
   c) an antibody comprising the heavy chain sequence of SEQ ID NO:41, 42, 43, 44, or 45 and the light chain sequence of SEQ ID NO:28;
   d) an antibody comprising the heavy chain sequence of SEQ ID NO:39, 40, 41, 42, 43, 44, or 45 and the light chain sequence of SEQ ID NO:27;

e) an antibody comprising the heavy chain sequence of SEQ ID NO:38 and the light chain sequence of SEQ ID NO:26;

f) an antibody comprising the heavy chain sequence of SEQ ID NO:37 and the light chain sequence of SEQ ID NO:25;

g) an antibody comprising a heavy chain $CDR_{H1}$ sequence of SEQ ID NO:1, a heavy chain $CDR_{H2}$ sequence of SEQ ID NO:7, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:22;

h) an antibody comprising a heavy chain $CDR_{H1}$ sequence of SEQ ID NO:1, a heavy chain $CDR_{H2}$ sequence of SEQ ID NO:9, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:22;

i) an antibody comprising a heavy chain $CDR_{H1}$ sequence of SEQ ID NO:1, a heavy chain $CDR_{H2}$ sequence of SEQ ID NO:4, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21;

j) an antibody comprising a heavy chain $CDR_{H1}$ sequence of SEQ ID NO:1, a heavy chain $CDR_{H2}$ sequence of SEQ ID NO:5, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21;

k) an antibody comprising a heavy chain $CDR_{H1}$ sequence of SEQ ID NO:1, a heavy chain $CDR_{H2}$ sequence of SEQ ID NO:6, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21;

l) an antibody comprising a heavy chain $CDR_{H1}$ sequence of SEQ ID NO:1, a heavy chain $CDR_{H2}$ sequence of SEQ ID NO:8, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21; and m) an antibody comprising a heavy chain $CDR_{H1}$ sequence of SEQ ID NO:1, a heavy chain $CDR_{H2}$ sequence of SEQ ID NO:9, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21.

2. The method of claim 1, wherein the subject has an elevated blood level of GDF15.

3. The method of claim 1, wherein the subject exhibits a glomerular filtration rate (GFR) below 90 ml creatinine/minute/1.73 $m^2$ body-surface area.

4. The method of claim 1, wherein the subject exhibits albuminuria.

5. The method of claim 1, wherein the subject exhibits urinary excretion of albumin in excess of 30 mg per day, 30 mg per liter of urine, and/or 30 pg/mg of creatinine in urine.

6. The method of claim 1, wherein the subject exhibits a serum uric acid level of at least 6.3 mg/dL.

7. The method of claim 1, wherein the subject exhibits iron deficiency.

8. The method of claim 1, wherein the subject exhibits transferrin saturation of below 25% and a low ferritin level.

9. The method of claim 1, wherein the anti-GDF15 antibody is humanized or human.

10. The method of claim 1, wherein the anti-GDF15 antibody comprises the heavy chain sequence of SEQ ID NO:47 and the light chain sequence of SEQ ID NO:30.

11. The method of claim 1, wherein the anti-GDF15 antibody comprises a heavy chain $CDR_{H1}$ sequence of SEQ ID NO:1, a heavy chain $CDR_{H2}$ sequence of SEQ ID NO: 7, and a heavy chain $CDR_{H3}$ sequence of SEQ ID NO:13; and a light chain $CDR_{L1}$ sequence of SEQ ID NO:16, a light chain $CDR_{L2}$ sequence of SEQ ID NO:18, and a light chain $CDR_{L3}$ sequence of SEQ ID NO:22.

12. The method of claim 1, wherein the anti-GDF15 antibody comprises the heavy chain sequence of SEQ ID NO:48 and the light chain sequence of SEQ ID NO:29.

13. The method of claim 1, wherein the anti-GDF15 antibody comprises a heavy chain $CDR_{H1}$ sequence of SEQ ID NO:1, a heavy chain $CDR_{H2}$ sequence of SEQ ID NO: 8, and a heavy chain $CDR_{H3}$ sequence of SEQ ID NO:13; and a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21.

14. A method of increasing renal function in a subject suffering from chronic kidney disease (CKD), the method comprising administering an effective amount of an anti-GDF15 antibody that decreases or inhibits GDF15 activity to increase renal function in the subject, wherein the anti-GDF15 antibody is selected from:

a) an antibody comprising the heavy chain sequence of SEQ ID NO:47 or 49 and the light chain sequence of SEQ ID NO:30;

b) an antibody comprising the heavy chain sequence of SEQ ID NO:41, 42, 43, 44, 45, 46, 48, or 49 and the light chain sequence of SEQ ID NO:29;

c) an antibody comprising the heavy chain sequence of SEQ ID NO:41, 42, 43, 44, or 45 and the light chain sequence of SEQ ID NO:28;

d) an antibody comprising the heavy chain sequence of SEQ ID NO:39, 40, 41, 42, 43, 44, or 45 and the light chain sequence of SEQ ID NO:27;

e) an antibody comprising the heavy chain sequence of SEQ ID NO:38 and the light chain sequence of SEQ ID NO:26;

f) an antibody comprising the heavy chain sequence of SEQ ID NO:37 and the light chain sequence of SEQ ID NO:25;

g) an antibody comprising a heavy chain $CDR_{H1}$ sequence of SEQ ID NO:1, a heavy chain $CDR_{H2}$ sequence of SEQ ID NO:7, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:22;

h) an antibody comprising a heavy chain $CDR_{H1}$ sequence of SEQ ID NO:1, a heavy chain $CDR_{H2}$ sequence of SEQ ID NO:9, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:22;

i) an antibody comprising a heavy chain $CDR_{H1}$ sequence of SEQ ID NO:1, a heavy chain $CDR_{H2}$ sequence of SEQ ID NO:4, and a heavy chain $CDR_{H3}$ sequence of SEQ ID NO:13; and
 a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21;

j) an antibody comprising a heavy chain $CDR_{H1}$ sequence of SEQ ID NO:1, a heavy chain $CDR_{H2}$ sequence of SEQ ID NO:5, and a heavy chain $CDR_{H3}$ sequence of SEQ ID NO:13; and
 a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21;

k) an antibody comprising a heavy chain $CDR_{H1}$ sequence of SEQ ID NO:1, a heavy chain $CDR_{H2}$ sequence of SEQ ID NO:6, and a heavy chain $CDR_{H3}$ sequence of SEQ ID NO:13; and
 a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21;

l) an antibody comprising a heavy chain $CDR_{H1}$ sequence of SEQ ID NO:1, a heavy chain $CDR_{H2}$ sequence of SEQ ID NO:8, and a heavy chain $CDR_{H3}$ sequence of SEQ ID NO:13; and
 a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21; and m) an antibody comprising a heavy chain $CDR_{H1}$ sequence of SEQ ID NO:1, a heavy chain $CDR_{H2}$ sequence of SEQ ID NO:9, and a heavy chain $CDR_{H3}$ sequence of SEQ ID NO:13; and
 a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21;

wherein the subject does not exhibit cachexia.

15. The method of claim 14, wherein the subject has an elevated blood level of GDF15.

16. The method of claim 14, wherein the subject exhibits a glomerular filtration rate (GFR) below 90 ml creatinine/minute/1.73 m$^2$ body-surface area.

17. The method of claim 14, wherein the subject exhibits albuminuria.

18. The method of claim 14, wherein the subject exhibits urinary excretion of albumin in excess of 30 mg per day, 30 mg per liter of urine, and/or 30 µg/mg of creatinine in urine.

19. The method of claim 14, wherein the subject exhibits hyperuricemia.

20. The method of claim 14, wherein the subject exhibits a serum uric acid level of at least 6.3 mg/dL.

21. The method of claim 14, wherein the subject exhibits iron deficiency.

22. The method of claim 14, wherein the subject exhibits transferrin saturation of below 25% and a low ferritin level.

23. The method of claim 14, wherein the anti-GDF15 antibody is humanized or human.

24. The method of claim 14, wherein the anti-GDF15 antibody comprises the heavy chain sequence of SEQ ID NO:47 and the light chain sequence of SEQ ID NO:30.

25. The method of claim 14, wherein the anti-GDF15 antibody comprises a heavy chain $CDR_{H1}$ sequence of SEQ ID NO:1, a heavy chain $CDR_{H2}$ sequence of SEQ ID NO: 7, and a heavy chain $CDR_{H3}$ sequence of SEQ ID NO:13; and a light chain $CDR_{L1}$ sequence of SEQ ID NO:16, a light chain $CDR_{L2}$ sequence of SEQ ID NO:18, and a light chain $CDR_{L3}$ sequence of SEQ ID NO:22.

26. The method of claim 14, wherein the anti-GDF15 antibody comprises the heavy chain sequence of SEQ ID NO:48 and the light chain sequence of SEQ ID NO:29.

27. The method of claim 14, wherein the anti-GDF15 antibody comprises a heavy chain $CDR_{H3}$ sequence of SEQ ID NO:1, a heavy chain $CDR_{H2}$ sequence of SEQ ID NO: 8, and a heavy chain $CDR_{H3}$ sequence of SEQ ID NO:13; and a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21.

* * * * *